US007166713B2

(12) United States Patent
Dass et al.

(10) Patent No.: US 7,166,713 B2
(45) Date of Patent: Jan. 23, 2007

(54) VARIANT CLEAVAGE STIMULATION FACTOR AND ITS ENCODING NUCLEIC ACID

(75) Inventors: Brinda Dass, Lubbock, TX (US); Clinton C. MacDonald, Lubbock, TX (US); Allison Michelle Wallace-Shannon, The Woodlands, TX (US)

(73) Assignee: Texas Techn University, Lubbock, TX (US)

( * ) Notice: Subject to any disclaimer, the term of this patent is extended or adjusted under 35 U.S.C. 154(b) by 282 days.

(21) Appl. No.: 10/314,519

(22) Filed: Dec. 9, 2002

(65) Prior Publication Data

US 2003/0215833 A1   Nov. 20, 2003

Related U.S. Application Data

(60) Provisional application No. 60/338,672, filed on Dec. 11, 2001.

(51) Int. Cl.
*C07H 21/04*  (2006.01)
*C12N 15/85*  (2006.01)

(52) U.S. Cl. .................. 536/23.1; 435/320.1; 435/325; 435/252.3; 435/235.1; 435/254.2

(58) Field of Classification Search ...................... None
See application file for complete search history.

(56) References Cited

U.S. PATENT DOCUMENTS 5,484,768 A   1/1996   Donahue et al.

FOREIGN PATENT DOCUMENTS

| WO | WO 92/00752 |   | 1/1992 |
| WO | WO 00/15799 | * | 3/2000 |
| WO | WO 01/53312 | * | 7/2001 |

OTHER PUBLICATIONS

NCBI Entrez Nucleotide database, Accession AY130299, GI: 24416590, Homo sapiens tCstF-64 (CSTF2T) mRNA, complete cds. Oct. 28, 2002.*
O'Brien et al., "Changes in Polyadenylation of Cation-Dependent Mannose 6-Phosphate Receptor During Spermatogenesis," Abstracts of papers presented at Thirty-First Annual Meeting of the American Society for Cell Biology, Boston, MA., *J. Cell Biol.* 115(3 Part 2):49A (1987).
de Luis et al., "Gene Expression of Mouse M1 and M2 Pyruvate Kinase Isoenzymes Correlates with Differential Poly(A) Tract Extension of their mRNAs During the Development of Spermatogenesis," *Biochimica et Biophysica Acta* 1396(3):294-305 (1998).
Standart et al., "Regulation of Translation by Specific Protein/mRNA Interactions," *Biochimie* 76(9):867-879 (1994).
Oyen et al., "Subunits of Cyclic Adenosine 3', 5'-Monophosphate-Dependent Protein Kinase Show Differential and Distinct Expression Patterns During Germ Cell Differentiation: Alternative Polyadenylation in Germ Cells Gives Rise to Unique Smaller-Sized mRNA Species," *Biology of Reproduction* 43(1):46-54 (1990).
Chennathukuzhi et al., "Increased Levels of the Polyadenylation/Cleavage Stimulatory Factor Cst 64 Facilitate the Cleavage at an Alternative 3' End-Processing Site of TB-RBP mRNAs in Male Germ Cells," *Biology of Reproduction* 60(SUPPL. 1):213 (1999) (abstract only).
Dass et al., "Overexpression of the CstF-64 and CPSF-160 Polyadenylation Protein Messenger RNAs in Mouse Male Germ Cells," *Biol. Reprod.* 64(6):1722-1729 (2001).
Lieberfarb et al., "Mutations that Perturb Poly(A)-Dependent Maternal mRNA Activation Block the Initiation of Development," *Development* 122(2):579-588 (1996).
Kashiwabara et al., "Identification of a Novel Isoform of Poly(A) Polymerase, TPAP, Specifically Present in the Cytoplasm of Spermatogenic Cells," *Development Biology* 228(1):106-115 (2000).
Jin et al., "Regulation of Cell Fate in *Caenorhabditis Elegans* by a Novel Cytoplasmic Polyadenylation Element Binding Protein," *Developmental Biology* 229(2):537-553 (2001).
Lee et al., "Developmentally Regulated Polyadenylation of Two Discrete Messenger Ribonucleic Acids for Mullerian Inhibiting Substance," *Endocrinology* 130(2):847-853 (1992).
Hiyoshi et al., "Isolation of cDNA for a Xenopus Sperm-Specific Basic Nuclear Protein (SP4) and Evidence for Expression of SP4 mRNA in Primary Spermatocytes," *Experimental Cell Research* 194(1):95-99 (1991).
Lee et al., "An Intronless gene Encoding a Poly(A) Polymerase is Specifically Expressed in Testis," *FEBS Letters* 487(2):287-292 (2000).
Walker et al., "RNA Processing and the Control of Spermatogenesis," *Frontiers of Hormone Research* 25:34-58 (1999).
Luitjens et al., "CPEB Proteins Control Two Key Steps in Spermatogenesis in *C. Elegans*," *Genes and Development* 14(20):2596-2609 (2000).
Mishima et al., "Regulation of ADP-Ribosylation Factor (ARF) Expression: Cross-Species Conservation of the Developmental and Tissue-Specific Alternative Polyadenylation of ARF 4 mRNA," *Journal of Biological Chemistry* 267(33):24109-24116 (1992).
Fujimoto et al., "Changes in Polyadenylation of Lactate Dehydrogenase-X mRNA During Spermatogenesis in Mice," *Molecular Reproduction and Development* 1(1):27-34 (1988).

(Continued)

*Primary Examiner*—Juliet C. Switzer
(74) *Attorney, Agent, or Firm*—Nixon Peabody LLP

(57) ABSTRACT

The present invention relates to an isolated human nucleic acid molecule encoding a protein or polypeptide which controls RNA polyadenylation, an isolated mouse nucleic acid molecule encoding a protein or polypeptide which controls RNA polyadenylation, and nucleic acid constructs, host cells and an expression system incorporating the nucleic acid molecules. The present invention also discloses methods of diagnosing male infertility; a method of contraception for mammals; and a method for diagnosing a cancerous condition in a subject using the nucleic acid molecules and proteins of the present invention.

8 Claims, 12 Drawing Sheets

OTHER PUBLICATIONS

Zhang et al., "Expression of Germ Cell Nuclear Factor (GCNF/RTR) During Spermatogenesis," *Molecular Reproduction and Development* 50(1):93-102 (1998).

Chennathukuzhi et al., "Elevated Levels of the Polyadenylation Factor CstF 64 Enhance Formation of the 1kB Testis Brain RNA-Binding Protein (TB-RBP) mRNA in Male Germ Cells," *Molecular Reproduction and Development* 58(4):460-469 (2001).

Wallace et al., "Two Distinct Forms of the 64,000 $M_r$ Protein of the Cleavage Stimulation Factor are Expressed in Mouse Male Germ Cells," *Proc. Natl. Acad. Sci USA* 96:6763-6768 (1999).

MacDonald et al., "Reexamining the Polyadenylation Signal: Were We Wrong About AAUAAA?" *Mol. Cell. Endocrinol.* 190:1-8 (2002).

Meijer et al., "Molecular Characterization of the Testis Specific c-abl mRNA in Mouse," *EMBO J.* 6(13):4041-4048 (1987).

Oppi et al., "Nucleotide Sequence of Testis-Derived c-abl cDNAs: Implications for Testis-Specific Transcription and abl Oncogene Activation," *Proc. Natl. Acad. Sci. USA* 84:8200-8204 (1987).

Foulkes et al., "Pituitary Hormone FSH Directs the CREM Functional Switch During Spermatogenesis," *Nature* 362:264-267 (1993).

Ravnik et al., "The Developmentally Restricted Pattern of Expression in the Male Germ Line of a Murine Cyclin A, Cyclin A2, Suggests Roles in Both Mitotic and Meiotic Cell Cycles," *Dev. Biol*, 173:69-78 (1996).

Edwalds-Gilbert et al., "Alternative Poly(A) Site Selection in Complex Transcription Units: Means to an End?" *Nucl. Acids Res.* 25(13):2547-2561 (1997).

Dass et al., "The Gene for a Variant Form of the Polyadenylation Protein CstF-64 is on Chromosome 19 and is Expressed in Pachytene Spermatocytes in Mice," *J. Biol. Chem.* 276(11):8044-8050 (2001).

Monesi, V., "Differential Rate of Ribonucleic Acid Synthesis in the Autosomes and Sex Chromosomes During Male Meiosis in the Mouse," *Chromosoma* 17:11-21 (1965).

McCarrey et al., "Human Testis-Specific PGK Gene Lacks Introns and Possesses Characteristics of a Processed Gene," *Nature* 326:501-505 (1987).

Handel et al., "Role of Sex Chromosomes in the Control of Male Germ-Cell Differentiation," *Ann. N.Y. Acad. Sci.* 637:64-73 (1991).

McCarrey et al., "Semiquantitative Analysis of X-Linked Gene Expression During Spermatogenesis in the Mouse: Ethidium-Bromide Staining of RT-PCR Products," *GATA* 9(4):117-123 (1992).

Calamera et al., "Male Antisperm Antibodies: Association with a Modified Sperm Stress Test and Lipid Peroxidation," *Andrologia* 34, 63-68 (2002).

Chiu et al., "Use of Antisperm Antibodies in Differential Display Western Blotting to Identify Sperm Proteins Important in Fertility," *Human Reproduction* 17(4):984-989 (2002).

Boman et al., "Newly Diagnosed Bladder Cancer: The Relationship of Initial Symptoms, Degree of Microhematuria and Tumor Marker Status," *J. Urology* 168(5):1955-1959 (2002).

Schadendorf D., "Gene-Based Therapy of Malignant Melanoma," *Seminars in Oncology* 29(5):503-512 (2002).

Takagaki et al., "The Human 64-kDa Polyadenylation Factor Contains a Ribonucleoprotein-type RNA Binding Domain and Unusual Auxiliary Motifs," *Proc. Natl. Acad. Sci. USA* 89(4):1403-1407 (1992).

McCarrey et al., "Construction and Preliminary Characterization of a Series of Mouse and Rat Testis cDNA Libraries," *J. Androl.* 20(5):635-639 (1999).

O'Brien, "Stage-Specific Protein Synthesis by Isolated Spermatogenic Cells Throughout Meiosis and Early Spermiogenesis in the Mouse," *Biol. Reprod.* 37(1):147-157 (1987).

MacDonald et al., "The 64-Kilodalton Subunit of the CstF Polyadenylation Factor Binds to Pre-mRNAs Downstream of the Cleavage Site and Influences Cleavage Site Location," *Mol. Cell. Biol.* 14(10):6647-6654 (1994).

Copeland et al., "Development and Applications of a Molecular Genetic Linkage Map of the Mouse Genome," *Trends Genet.* 7(4):113-118 (1991).

Watanabe-Fukunaga et al., "The cDNA Structure, Expression, and Chromosomal Assignment of the Mouse Fas antigen," *J. Immunol.* 148(4):1274-1279 (1992).

Wilkie et al., "Evolution of the Mammalian G Protein α Subunit Multigene Family," *Nat. Genet.* 1(2):85-91 (1992).

Wilusz et al., "A 64 kd Nuclear Protein Binds to RNA Segments that Include the AAUAAA Polyadenylation Motif," *Cell* 52(2):221-228 (1988).

Takagaki et al., "A Multisubunit Factor, CstF, is Required for Polyadenylation of Mammalian Pre-mRNAs," *Genes Dev.* 4:2112-2120 (1990).

Takagaki et al., "Levels of Polyadenylation Factor CstF-64 Control IgM Heavy Chain mRNA Accumulation and Other Events Associated With B Cell Differentiation," *Mol. Cell* 2:761-771 (1998).

Ishikawa et al., "Prediction of the Coding Sequences of Unidentified Human Genes. X. The Complete Sequences of 100 New cDNA Clones from Brain Which Can Code for Large Proteins *in vitro*," *DNA Res.* 5(3):169-176 (1998).

Hatton et al., "The Drosophila Homologue of the 64 kDa Subunit of Cleavage Stimulation Factor Interacts with the 77 kDa Subunit Encoded by the Suppressor of Forked Gene," *Nucleic Acids Res.* 28(2):520-526 (2000).

Barbaux et al., "The *Xenopus laevis* Homologue of the 64-kDa Subunit of Cleavage Stimulation Factor," *Comp. Biochem. Physiol.* 114B(3):313-315 (1996).

Burd et al., "Conserved Structures and Diversity of Functions of RNA-Binding Proteins," *Science* 265:615-621 (1994).

Nagai et al., "Crystal Structure of the RNA-Binding Domain of the U1 Small Nuclear Ribonucleoprotein A," *Nature* 348:515-520 (1990).

Nagata et al., "Structure and Interactions with RNA of the N-Terminal UUAG-Specific RNA-Binding Domain of hnRNP D0," *J. Mol. Biol.* 287(2):221-237 (1999).

Takagaki et al., "Complex Protein Interactions Within the Human Polyadenylation Machinery Identify a Novel Component," *Mol. Cell Biol.* 20(5):1515-1525 (2000).

Richardson et al., "MEARA Sequence Repeat of Human CstF-64 Polyadenylation Factor is Helical in Solution. A Spectroscopic and Calorimetric Study," *Biochemistry* 38(39):12869-12875 (1999).

Beyer et al., "RNA Ligands Selected by Cleavage Stimulation Factor Contain Distinct Sequence Motifs that Function as Downstream Elements in 3'-End Processing of Pre-mRNA," *J. Biol. Chem.* 272(42):26769-26779 (1997).

Takagaki et al., "RNA Recognition by the Human Polyadenylation Factor CstF," *Mol. Cell Biol.* 17(7):3907-3914 (1997).

Evans et al., "A Complex Containing CstF-64 and the SL2 snRNP Connects mRNA 3' End Formation and *Trans*-Splicing in C. Elegans Operons," *Genes Dev.* 15:2562-2571 (2001).

Dass et al., "The Gene *CSTF2T*, Encoding the Human Varian CstF-64 Polyadenylation Protein τCstF-64, Lacks Introns and May Be Associated with Male Sterility," *Genomics* 80(5):1-6 (2002).

Calvo et al., "Evolutionarily Conserved Interaction Between CstF-64 and PC4 Links Transcription, Polyadenylation, and Termination," *Mol. Cell* 7:1013-1023 (2001).

Wang et al., "An Abundance of X-Linked Genes Expressed in Spermatogonia," *Nature Genetics* 27:422-426 (2001).

Boer et al., "The Testis-Specific Phosphoglycerate Kinase Gene *pgk2* is a Recruited Retroposon," *Mol. Cell Biol.* 7:3107-3112 (1987).

Dahl et al., "A Testis-Specific Form of the Human Pyruvate Dehydrogenase Elα Subunit is Coded for by an Intronless Gene on Chromosome 4," *Genomics* 8:225-232 (1990).

Hendriksen et al., "Testis-Specific Expression of a Functional Retroposon Encoding Glucose-6-Phosphate Dehydrogenase in the Mouse," *Genomics* 41:350-359 (1997).

Ehrmann et al., "Characterization of Genes Encoding Translation Initiation Factor eIF-2γ in Mouse and Human: Sex Chromosome Localization, Escape from X-Inactivation and Evolution," *Hum. Mol. Genet.* 7(11):1725-1737 (1998).

Sedlacek et al, "Human and Mouse XAP-5 and XAP-5-Like (X5L) Genes: Identification of an Ancient Functional Retroposon Differentially Expressed in Testis," *Genomics* 61:125-132 (1999).

Elliott et al., "An Evolutionarily Conserved Germ Cell-Specific hnRNP is Encoded by a Retrotransposed Gene," *Hum. Mol. Genet.* 9(14):2117-2124 (2000).

Lingenfelter et al., "Expression and Conservation of Processed Copies of the RBMX Gene," *Mamm. Gen.* 12:538-545 (2001).

Wang et al., "Functional Substitution for $TAF_{11}250$ by a Retroposed Homolog that is Expressed in Human Spermatogenesis," *Hum. Mol. Genet.* 11(19):2341-2346 (2002).

Samiotaki et al., "Assignment of the 160-kDa Subunit of Cleavage and Polyadenylation Specificity Factor (CPSF1) to Human Chromosome 8q24.23 by Radiation Hybrid Mapping," *Cytogenet. Cell. Genet.* 90:234-235 (2000).

Samiotaki et al., "Assignment of the 100-kDa Subunit of Cleavage and Polyadenylation Specificity Factor (CPSF2) to Human Chromosome 14q31.3 by Radiation Hybrid Mapping," *Cytogenet. Cell. Genet.* 90:328-329(2000).

* cited by examiner

```
1   MAGLTVRDPAVDRSLRSVFVGNIPYEATEEQLKDIFSEVGPVVSFRLVYD                    50
1   MSSLAVRDPAMDRSLRSVFVGNIPYEATEEQLKDIFSEVGSVFSFRLVYD

51  RETGKPKGYGFCEYQDQETALSAMRNLNGREFSGRALRVDNAASEKNKEE                   100
51  RETGKPKGYGFCEYQDQETALSAMRNLNGREFSGRALRVDNAASEKNKEE

101 LKSLGTGAPVIESPYGETISPEDAPESISKAVASLPPEQMFELMKQMKLC                   150
101 LKSLGPAAPIIDSPYGDPIEDAPESITRAVASLPPEQMFELMKQMKLC

151 VQNSPQEARNMLLQNPQLAYALLQAQVVMRIVDPEIALKILHRQTNIPTL                   200
151 VQNSHQEARNMLLQNPQLAYALLQAQVVMRIMDPEIALKILHRKIHVTPL

201 IAGNPQPVHGAG------PG--SGSNVSMNQQNPQAPQAQS                           250
201 IPGKSQPVSGPGLVGWASGLAAGPAPAPGLCPGPNVMLNQQNPPAPQPQH
```

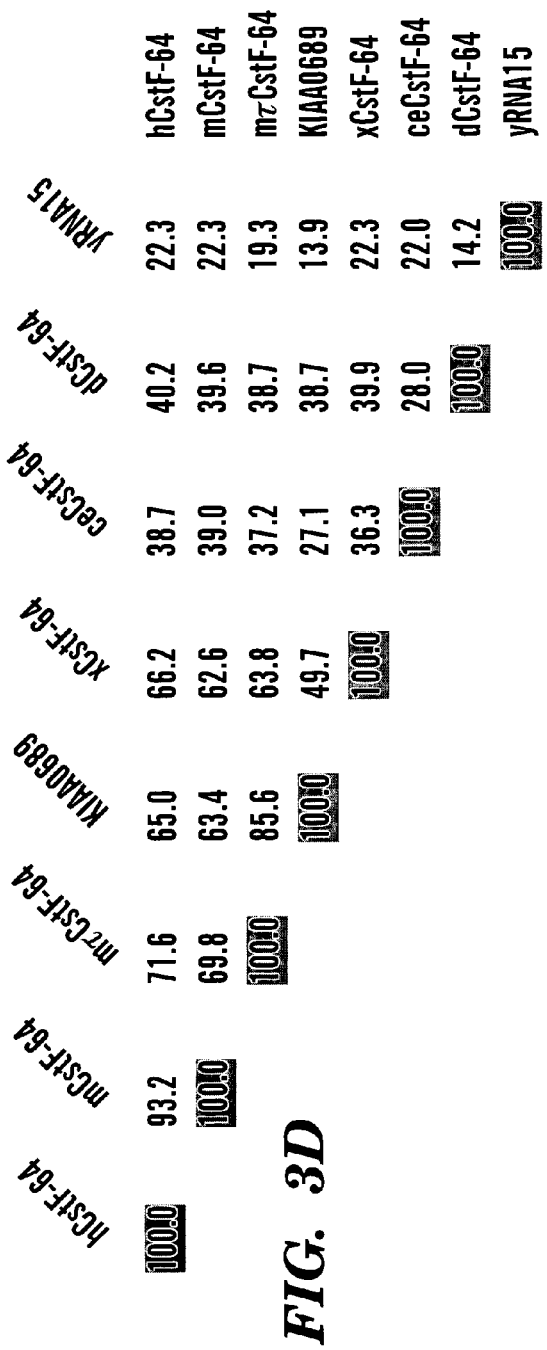
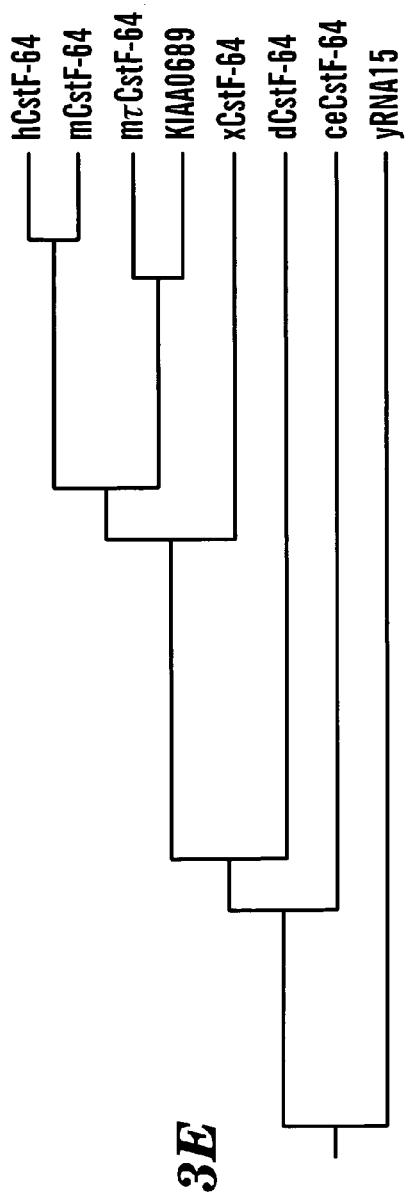
FIG. 3D
FIG. 3E

FIG. 4A

```
                10         20         30         40         50
  1 MSSLAVRDPAMDRSLRSVFVGNIPYEATEEQLKDIFSEVGSVVSFRLVYD    hrCstF-64
  1 MSSLAVRDPAMDRSLRSVFVGNIPYEATEEQLKDIFSEVGSVVSFRLVYD    mrCstF-64

60         70         80         90        100
 51 RETGKPKGYGFCEYQDQETALSAMRNLNGREFSGRALRVDNAASEKNKEE    hrCstF-64
 51 RETGKPKGYGFCEYQDQETALSAMRNLNGREFSGRALRVDNAASEKNKEE    mrCstF-64

110        120        130        140        150
101 LKSLGPAAPIIDSPYGDPIDPEDAPESITRAVASLPPEQMFELMKQMKLC    hrCstF-64
101 LKSLGPAAPIIDSPYGDPIDPEDAPESITRAVASLPPEQMFELMKQMKLC    mrCstF-64

160        170        180        190        200
151 VQNSHQEARNMLLQNPQLAYALLQAQVVMRIMDPEIALKILHRKIHVTPL    hrCstF-64
151 VQNSHQEARNMLLQNPQLAYALLQAQVVMRIMDPEIALKILHRKIHVTPL    mrCstF-64

210        220        230        240        250
201 IPGKSQSVSVSG---------PGPGPGPGLCPGPNVLLNQQNPPAPQPQH    hrCstF-64
201 IPGKSQPVSGPGLVGWASGLAAGPAPAPGLCPGPNVMLNQQNPPAPQPQH    mrCstF-64

260        270        280        290        300
242 IARRPVKDIPPLMQTPIQGGIPAPGPIPAAVPGAGPGSLTPGGAMQPQLG    hrCstF-64
251 LPRRPVKDIPPLMQTSIQGGIPAPGPIPAAVPGPGPGSLTPGGAMQPQVG    mrCstF-64

310        320        330        340        350
252 MPGVGPVPLERGQVQMSDPRAPIPRGFVTPGGLPPRGLLGDAPNDPRGGT    hrCstF-64
301 MPVVGPVPLERGQMQTSDPRPPMPRGPMPSGGIPPRGLLGDAPNDPRGGT    mrCstF-64

360        370        380        390
342 LLSVTGEVEPRGYLGPPHQGPPMHHASGHDTRGPSSHEMRGGPLG-DPRL    hrCstF-64
351 LLSVTGEVEPRGYMGPPHQGPPMHH--GHDNRGPASHDMRGGPLAADPRM    mrCstF-64

400        410        420        430        440
391 LIGEPRGPMIDQRGLPMDGRGGRDSRAMETRAMETEVLETRVMERRGMET    hrCstF-64
399 LIGEPRGPMIDQRGLPMDGRGGRESRGMETRPMETEVLEPRGMERR-MET    mrCstF-64

450        460        470        480        490
441 CAMETRGMEARGMDARGLEMRGPVPSSRGPMTGGIQGPGPINIGAGGPPQ    hrCstF-64
443 CAMETRG-----MDARGLEMRGPGPSSRGPMTGGIQGPGPINMGAGGP-Q    mrCstF-64

500        510        520        530        540
491 GPRQVPGISGVGNPGAGMQGIGIQGIGMQGAGIQGGGMQGAGIQGVSIQG    hrCstF-64
492 GPRQVPNIAGVGNPGGTMQGAGIQGGGMQGAGMQGGGMQGAGMQGGGMQG    mrCstF-64

550        560        570        580        590
541 -------------GGIQGGGIQGASKQGGSQPSSFSPGQSQVTPQDQEKA    hrCstF-64
542 AGMQAGMQGASMQGGMQGAGMQGASKQGGGQPSSFSPGQSQVTPQDQEKA    mrCstF-64

600        610        620        630
578 ALIMQVLQLTADQIAMLPPEQRQSILILKEQIQKSTGAS    hrCstF-64
592 ALIMQVLQLTADQIAMLPPEQRQSILILKEQIQKSTGAS    mrCstF-64
```

VARIANT CLEAVAGE STIMULATION FACTOR AND ITS ENCODING NUCLEIC ACID

This application claims the benefit of U.S. Provisional Patent Application Ser. No. 60/338,672, filed Dec. 11, 2001.

The subject matter of this application was made with support from the United States Government under The National Institutes of Health, Grant No. 1 R01 HD37109-01A1. The U.S. Government may have certain rights.

FIELD OF THE INVENTION

The present invention relates to an isolated nucleic acid molecule encoding a variant of the human cleavage stimulation factor (hCstF-64) polyadenylation protein, hτCstF-64; an isolated mouse nucleic acid molecule encoding the variant of the murine cleavage stimulation factor (mCstF-64) polyadenylation protein, mτCstF-64; and methods of use for the nucleic acid molecules and the proteins in diagnosis and treatment of male infertility.

BACKGROUND OF THE INVENTION

Polyadenylation is the process of eukaryotic mRNA processing in which 3' end cleavage occurs, followed by the addition of as many as 250 adenosine residues. Messenger RNA polyadenylation is important for cellular processes including transcription termination, splicing, mRNA transport, translation, and mRNA stability. Polyadenylation requires at least five protein complexes, including the cleavage and polyadenylation specificity factor (CPSF), the cleavage stimulation factor (CstF), two cleavage factors (CFI and CFII), and the poly (A) polymerase. Other factors, including the poly(A)-binding protein II (which mediates poly7(A) tail length), the U1A small nuclear ribonucleoprotein (SnRNP) (which interacts with both CPSF and the poly(A)polymerase) and DSEF-1 (which binds G-rich auxiliary elements), also contribute to efficient polyadenylation.

In the past, it was believed that efficient polyadenylation required the sequence AAUAAA near the 3' end. More recent studies have brought this belief into question. Computer-aided surveys of sequences available in GenBank and other online datasets have suggested that the incidence of AAUAAA in mRNA 3' ends of certain tissues is far lower than previously suspected (reviewed in MacDonald et al., "Reexamining the Polyadenylation Signal: Were We Wrong About AAUAAA?" *Mol. Cell. Endocrinol.* 190:1–8 (2002)). The lower incidence of AAUAAA is especially notable in mRNAs from male germ cells of several mammalian species (Meijer et al., "Molecular Characterization of the Testis Specific c-abl mRNA in Mouse," *EMBO J.* 6:4041–4048 (1987); Oppi et al., "Nucleotide Sequence of Testis-Derived c-abl cDNAs: Implications for Testis-Specific Transcription and abl Oncogene Activation," *Proc. Natl. Acad. Sci. USA* 84:8200–8204 (1987); Øyen et al., "Subunits of Cyclic Adenosine 3',5'-Monophosphate-Dependent Protein Kinase Show Differential and Distinct Expression Patterns During Germ Cell Differentiation: Alternative Polyadenylation in Germ Cells Gives Rise to Unique Smaller-Sized mRNA Species," *Biol. Reprod.* 43:46–54 (1990); Wallace et al., "Two Distinct Forms of the 64,000 Mr Protein of the Cleavage Stimulation Factor are Expressed in Mouse Male Germ Cells," *Proc. Natl. Acad. Sci. USA* 96:6763–6768 (1999)). Moreover, there have been a number of reports of alternative polyadenylation in germ cells, in which one site is used in most somatic tissues, but a different site is used in germ cells (Meijer et al., "Molecular Characterization of the Testis Specific c-abl mRNA in Mouse," *EMBO J.* 6:4041–4048 (1987); Oppi et al., "Nucleotide Sequence of Testis-Derived c-abl cDNAs: Implications for Testis-Specific Transcription and abl Oncogene Activation," *Proc. Natl. Acad. Sci. USA* 84:8200–8204 (1987); Foulkes et al., "Pituitary Hormone FSH Directs the CREM Functional Switch During Spermatogenesis," *Nature* 362:264–267 (1993); Ravnik et al., "The Developmentally Restricted Pattern of Expression in the Male Germ Line of a Murine Cyclin A, Cyclin A2, Suggests Roles in Both Mitotic and Meiotic Cell Cycles," *Dev. Biol.* 173:69–78 (1996); Edwalds-Gilbert et al., "Alternative Poly(A) Site Selection in Complex Transcription Units: Means to an End?" *Nucl. Acids Res.* 25:2547–2561 (1997)). Together, these data argue strongly for a modified polyadenylation mechanism in male germ cells.

In studying AAUAAA-independent polyadenylation in mice, it was determined that there were two distinct forms of the essential polyadenylation protein CstF-64 (Cleavage stimulation Factor, 64,000 $M_r$) in male germ cells (Wallace et al., "Two Distinct Forms of the 64,000 $M_r$ Protein of the Cleavage Stimulation Factor are Expressed in Mouse Male Germ Cells," *Proc. Natl. Acad. Sci. USA* 96:6763–6768 (1999)). One form of CstF-64 was expressed in nuclei of cells in every tissue examined, and is referred to as the somatic CstF-64. This protein was expressed from a gene on the X chromosome in both mice (gene designation Cstf2) and humans (CSTF2). The other form was found only in male germ cells and brain, and is referred to as the variant CstF-64, or τCstF-64 (Wallace et al., "Two Distinct Forms of the 64,000 $M_r$ Protein of the Cleavage Stimulation Factor are Expressed in Mouse Male Germ Cells," *Proc. Natl. Acad. Sci. USA* 96:6763–6768 (1999); Dass et al., "The Gene for a Variant Form of the Polyadenylation Protein CstF-64 is on Chromosome 19 and is Expressed in Pachytene Spermatocytes in Mice," *J. Biol. Chem.* 276: 8044–8050 (2001)). Because genes on the X and Y chromosomes are inactivated during male meiosis (Monesi, V., "Differential Rate of Ribonucleic Acid Synthesis in the Autosomes and Sex Chromosomes During Male Meiosis in the Mouse," *Chromosoma* 17:11–21 (1965); McCarrey et al., "Human Testis-Specific PGK Gene Lacks Introns and Possesses Characteristics of a Processed Gene," *Nature* 326:501–504 (1987); Handel et al., "Role of Sex Chromosomes in the Control of Male Germ-Cell Differentiation," *Ann. NY Acad. Sci.* 637:64–73 (1991); McCarrey et al., "Semiquantitative Analysis of X-Linked Gene Expression During Spermatogenesis in the Mouse: Ethidium-Bromide Staining of RT-PCR Products," *Genetics Analysis Technology and Applications* 9:117–123 (1992)), it was proposed that the somatic CstF-64 was inactivated during pachytene of male meiosis due to sequestration of the X and Y chromosomes within the sex body (Wallace et al., "Two Distinct Forms of the 64,000 $M_r$ Protein of the Cleavage Stimulation Factor are Expressed in Mouse Male Germ Cells," *Proc. Natl. Acad. Sci. USA* 96:6763–6768 (1999)), and that τCstF-64 was a paralogous gene expressed from an autosome.

It seemed likely that this phenomenon was true not only of rodents (Wallace et al., "Two Distinct Forms of the 64,000 $M_r$ Protein of the Cleavage Stimulation Factor are Expressed in Mouse Male Germ Cells," *Proc. Natl. Acad. Sci. USA* 96:6763–6768 (1999), but of all eutherian mammals (Handel et al., "Role of Sex Chromosomes in the Control of Male Germ-Cell Differentiation," *Ann. NY Acad. Sci.* 637:64–73

(1991)), suggesting the presence and potential importance of τCstF-64 in human spermatogenesis.

The further identification and characterization of these RNA polyadenylation proteins in mammals and the genes that encode them is now needed to provide a greater understanding of the mechanisms underlying RNA processing in specialized cells, including germ cells, and to provide diagnostic tools and therapeutic treatment for the disorders related to the absence, or improper functioning, of these genes and the proteins or polypeptides they encode.

The present invention is directed at overcoming these and other deficiencies in the art.

SUMMARY OF THE INVENTION

The present invention relates to an isolated human nucleic acid molecule encoding a protein or polypeptide which controls RNA polyadenylation. The nucleic acid molecule is a variant of a somatic nucleic acid molecule and is functional when the somatic nucleic acid molecule is not functional.

The present invention also relates to: nucleic acid constructs, an expression system, and host cells containing the isolated human nucleic acid molecule of the present invention; the isolated protein or polypeptide encoded by the isolated human nucleic acid molecule; and methods of diagnosing male infertility, providing contraception for mammals, and diagnosing a cancerous condition in a subject using the isolated human nucleic acid molecule encoding a protein or polypeptide which controls RNA polyadenylation, or the protein it encodes.

Another aspect of the present invention is an isolated mouse nucleic acid molecule encoding a protein or polypeptide which controls RNA polyadenylation. The nucleic acid molecule is a variant of a somatic nucleic acid molecule and is functional when the somatic nucleic acid molecule is not functional.

The present invention also relates to nucleic acid constructs, an expression system, and host cells containing the isolated mouse nucleic acid molecule of the present invention.

Improper polyadenylation of proteins is known to be directly related to a variety of disease conditions and disorders. In the case of the variant CstF-64, a greater understanding of the gene and its encoded protein may provide a much needed tool to understanding cell development, alternative methods of polyadenylation of proteins, and supply a means to regulate male fertility.

BRIEF DESCRIPTION OF THE DRAWINGS

FIGS. 3A–E are comparisons of the protein encoded by the mτCstF-64 cDNA and other known forms of CstF-64. FIGS. 3A–C show an alignment of the mτCstF-64 protein (bottom line) with the hCstF-64 protein (top line). Alignment was by the CLUSTAL V method. Numbering is according to the mτCstF-64 sequence. Amino acids that differ from the human Cst-F-64 are boxed. Significant features: RNA-binding domain (RBD)(17-92), MEARA repeats (425–464), C-terminal domain (589–630), are boxed in gray. Inserted segments in mτCstF-64 relative to hCstF-64 are indicated by a black overline. The region thought to interact with CstF-77 is indicated by a gray overline. Boxed segments of the human sequence represent the regions of interaction for the 6A9 (332–427) and 3A7 (441–583) antibodies. FIG. 3D shows sequence identities (in percent) of known CstF-64 homologs. Shown are sequences from human (hCstF-64), mouse (mCstF-64), mouse τCstF-64 (mτCstF-64), human brain (KIAA0689), Xenopus laevis (xCstF-64), Drosophila melanogaster (dmCstF-64), Caenorhabditis elegans (ceCstF-64), and Saceha101myces cerevisice (yRNA15). Pairwise identities were determined from the alignments by CLUSTAL V method. FIG. 3E is a tree diagram showing the relative similarities of the human, mouse, bovine, Xenopus, Caenorhabditis, Drosophila, and yeast homologs of CstF-64.

FIGS. 4A–C are comparisons of human τCstF-64 protein sequence to known CstF-64 homologs. FIG. 4A is a protein sequence alignment of human τCstF-64 (top line) and mτCstF-64 (bottom line). Alignment was by the CLUSTAL V method. Numbering is according to the mτCstF-64 sequence. Amino acids in hτCstF-64 that differ from mτCstF-64 are boxed, as is the proline→serine$_{41}$ change shared between mouse and human τCstF-64s. Significant features (RBD, 17–92; MEARA repeats, 418–462; C-terminal domain, 575–616) are boxed in gray. A black overline indicates inserted segments in hτCstF-64 relative to human and mouse CstF-64. A gray overline indicates the region thought to interact with CstF-77. Gray boxes over the sequence indicate insertions in hτCstF-64 relative to mτCstF-64. FIG. 4B shows sequence identities (in percent) of known CstF-64 homologs. Shown are sequences from human (hCstF-64), mouse (mCstF-64), bovine (bovCstF-64, accession number AY130297), human τCstF-64 (hτCstF-64), mouse τCstF-64 (mτCstF-64), bovine τCstF-64 (bovτCstF-64, accession number AY130298), Xenopus laevis (xCstF-64), Drosophila melanogaster (dmCstF-64), Caenorhabditis elegans (ceCstF-64), and Saccharomyces cerevisiae (yRNA15). Pairwise identities were determined from the alignments by CLUSTAL V method. FIG. 4C is a tree diagram showing the relative similarities of the human, mouse, bovine, Xenopus, Caenorhabditis, Drosophila, and yeast homologs of CstF-64.

DETAILED DESCRIPTION OF THE INVENTION

Figure 1:
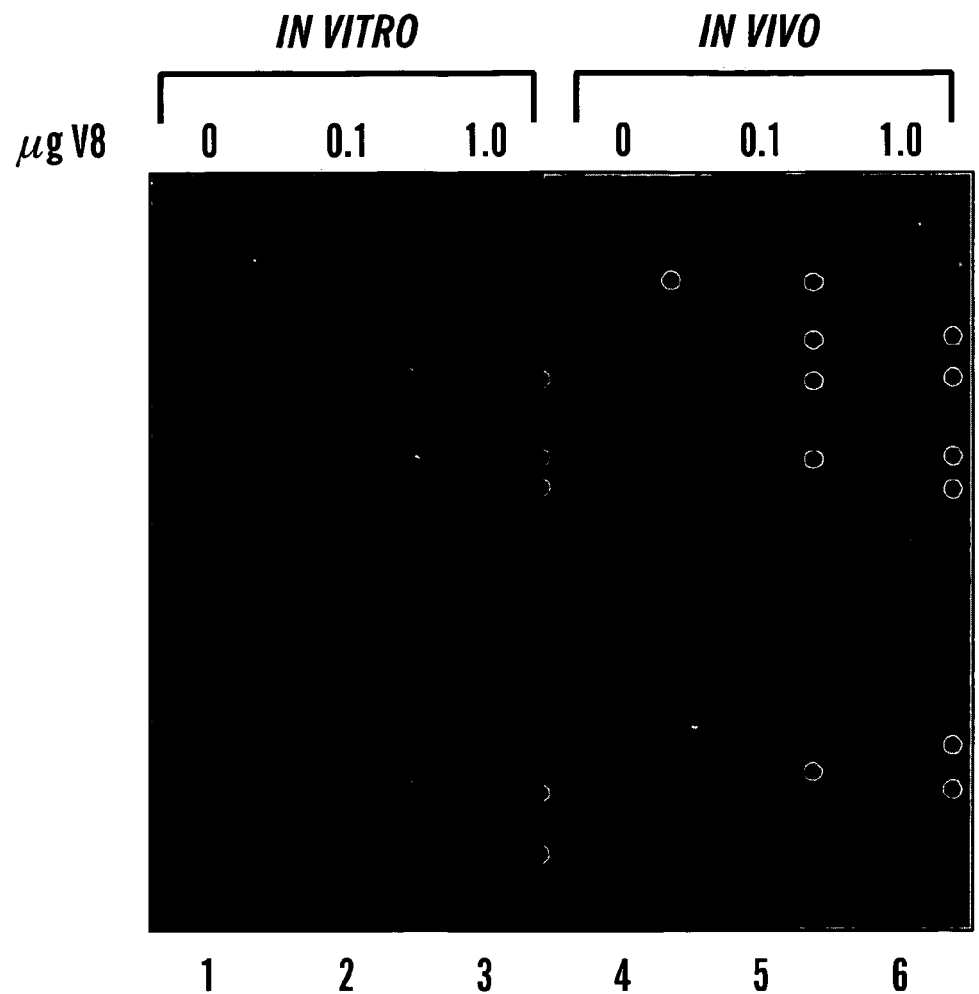
FIG. 1 is a partial V8 protease mapping of the protein encoded by mτCstF-64 (in vitro) and the variant Cst-F-64 protein (in vivo). Protein made in the reticulocyte lysate system (lanes 1–3, (in vitro) or immunoprecipitated from adult mouse seminiferous tubule extracts (lanes 4–6, in vivo) were treated with the indicated amounts of V8 protease. Dots indicate bands common to the in vivo and in vitro samples.

The present invention relates to an isolated human nucleic acid molecule encoding a protein or polypeptide which controls RNA polyadenylation. The nucleic acid molecule is a variant of a somatic nucleic acid molecule and is functional when the somatic nucleic acid molecule is not functional. One form of the nucleic acid molecule of the present invention, identified herein as CSTF2T, is isolated from human testis, and has a nucleotide sequence of SEQ ID NO: 1 as follows:

```
ggcacgagcc gctatcggct gtctgcacaa ccggaatcat gtcgagtttg gcggtgagag   60
acccggcaat ggatcgatca ctgcgttccg tgttcgtggg gaacattcca tatgaggcaa  120
ctgaggagca gttaaaggac attttctcgg aggttggttc tgttgtcagt ttccggctgg  180
tatacgatag agagacggga aaacccaagg gctatggctt ctgcgaatac caagaccagg  240
agaccgcgct tagtgccatg cggaacctca atgggcggga gttcagtggg agagcgcttc  300
gggtggacaa tgctgccagt gaaaagaata aggaggagtt aaagagcctt gggcctgcag  360
cgcccattat tgactcaccc tatgggggatc ccatcgatcc agaagatgcc cctgaatcga  420
ttaccagagc agtagccagt ctcccccccgg agcagatgtt tgagctgatg aagcagatga  480
agctctgtgt ccaaaacagc caccaggaag ctcgaaacat gttacttcaa aatccacaac  540
tggcttatgc actgttgcag gcacaagtag tgatgagaat catggatcca gagattgctc  600
tgaaaattct gcatcggaag atacatgtca caccactgat cccaggcaaa tctcagtctg  660
tgtctgtctc tggccctggc cctggccctg gccctgggct ctgcccagga cctaatgttc  720
tgctgaacca gcagaatcct ccagctcctc agcctcagca tttggctaga agacctgtga  780
aggacattcc tcctctgatg cagactccta tccagggtgg aattccagct ccagggccaa  840
taccagctgc agttcccgga gctggtcctg gttccttaac tcctggagga gcaatgcagc  900
cccaacttgg aatgccaggg gttggcccag tgcctttaga gcggggacaa gtgcagatgt  960
cagatcctag agctcctata cctgcgggac ccgtgactcc tggtggtctg cctcctcgag 1020
gactgttagg agatgctcca aatgacccac gtggagggac tttgctttca gtcactggag 1080
aagtggagcc cagaggttat ctgggtccac cccatcaggg tccccccatg catcatgcct 1140
ctggtcatga cactcgtggc ccttcctcac atgagatgag gggagggcca ttaggagatc 1200
ccagactgct aattggagag cccagaggcc ccatgataga tcaaagggt ctacctatgg 1260 atggtagagg tggtagagat tctcgagcga tggagactcg tgccatggaa actgaggtct 1320
tagagacacg tgtaatggag aggagaggaa tggagacctg tgcgatggaa accagaggga 1380
tggaagcaag gggcatggat gcaagaggat tggagatgag gggccctgtc cccagttcaa 1440
gaggccctat gactggtgga attcagggtc ctggtcccat taatataggg gcaggtggcc 1500
ctcctcaggg acccagacag gtcccaggca tttcaggggt ggggaatcct ggagctggta 1560
tgcagggtac aggcatacaa ggaacaggca tgcagggagc aggcatacaa ggaggaggga 1620
tgcagggggc aggcatacaa ggagtcagta tacaaggagg aggtatacaa ggaggaggta 1680
```

-continued

```
tacaggggc  aagcaagcaa  ggtggaagcc  agcctagcag  ttttagtcct  gggcagagcc  1740
aggtcactcc  acaggatcag  gagaaggcag  ctttgatcat  gcaggttctt  caactgactg  1800
cagatcagat  tgccatgctg  cccctgagc  aaaggcagag  tatcctgatt  ttaaaggaac  1860
aaatccagaa  atccactgga  gcgtcttgaa  aggttttaga  aaatatttgg  ctgtagtctc  1920
aaattttatt  ctgtagcatg  gagaatgggt  gcaaaaagct  gacttctgta  tccccacact  1980
tggattaggg  tttccctcct  cctagaacct  aatcttattt  tttgttcttt  ttctttcttt  2040
ctgttttcct  tttttttaa  ttgagggtgg  ggggaggagg  gagtgcgtct  gttcacttta  2100
agttacttta  aaataactct  gaacatgatt  atattatgcc  aaataagatt  acaaagaata  2160
agcagcaata  ttgaagcatc  tacagtatgt  taactacatt  ttttaaatgt  cgagtaaaac  2220
ttcgtgaaaa  ctgctcataa  agactaaaag  ttgacctgtt  aaaacgttaa  tgtactaaga  2280
tagttttaag  attttttggtt  gtataacaaa  ataaaagttt  acccaaaaaa  aaaaaaaaaa  2340
a                                                                      2341
```

The nucleic acid sequence corresponding to SEQ ID NO: 1 encodes a variant of human CstF-64, identified herein as hτCstF-64, having a deduced amino acid sequence corresponding to SEQ ID NO: 2, as follows:

```
Met Ser Ser Leu Ala Val Arg Asp Pro Ala Met Asp Arg Ser Leu Arg
 1               5                  10                  15
Ser Val Phe Val Gly Asn Ile Pro Tyr Glu Ala Thr Glu Glu Gln Leu
                20                  25                  30
Lys Asp Ile Phe Ser Glu Val Gly Ser Val Val Ser Phe Arg Leu Val
            35                  40                  45
Tyr Asp Arg Glu Thr Gly Lys Pro Lys Gly Tyr Gly Phe Cys Glu Tyr
        50                  55                  60
Gln Asp Gln Glu Thr Ala Leu Ser Ala Met Arg Asn Leu Asn Gly Arg
65                  70                  75                  80
Glu Phe Ser Gly Arg Ala Leu Arg Val Asp Asn Ala Ala Ser Glu Lys
                85                  90                  95
Asn Lys Glu Glu Leu Lys Ser Leu Gly Pro Ala Ala Pro Ile Ile Asp
            100                 105                 110
Ser Pro Tyr Gly Asp Pro Ile Asp Pro Glu Asp Ala Pro Glu Ser Ile
        115                 120                 125
Thr Arg Ala Val Ala Ser Leu Pro Pro Glu Gln Met Phe Glu Leu Met
    130                 135                 140
Lys Gln Met Lys Leu Cys Val Gln Asn Ser His Gln Glu Ala Arg Asn
145                 150                 155                 160
Met Leu Leu Gln Asn Pro Gln Leu Ala Tyr Ala Leu Leu Gln Ala Gln
                165                 170                 175
Val Val Met Arg Ile Met Asp Pro Glu Ile Ala Leu Lys Ile Leu His
            180                 185                 190
Arg Lys Ile His Val Thr Pro Leu Ile Pro Gly Lys Ser Gln Ser Val
        195                 200                 205
Ser Val Ser Gly Pro Gly Pro Gly Pro Gly Leu Cys Pro Gly
    210                 215                 220
Pro Asn Val Leu Leu Asn Gln Gln Asn Pro Ala Pro Gln Pro Gln
225                 230                 235                 240
His Leu Ala Arg Arg Pro Val Lys Asp Ile Pro Pro Leu Met Gln Thr
                245                 250                 255
```

-continued

```
Pro Ile Gln Gly Gly Ile Pro Ala Pro Gly Pro Ile Pro Ala Ala Val
            260                 265                 270
Pro Gly Ala Gly Pro Gly Ser Leu Thr Pro Gly Gly Ala Met Gln Pro
        275                 280                 285
Gln Leu Gly Met Pro Gly Val Gly Pro Val Pro Leu Glu Arg Gly Gln
        290                 295                 300
Val Gln Met Ser Asp Pro Arg Ala Pro Ile Pro Arg Gly Pro Val Thr
305                 310                 315                 320
Pro Gly Gly Leu Pro Pro Arg Gly Leu Leu Gly Asp Ala Pro Asn Asp
                325                 330                 335
Pro Arg Gly Gly Thr Leu Leu Ser Val Thr Gly Glu Val Glu Pro Arg
                340                 345                 350
Gly Tyr Leu Gly Pro Pro His Gln Gly Pro Pro Met His His Ala Ser
            355                 360                 365
Gly His Asp Thr Arg Gly Pro Ser Ser His Glu Met Arg Gly Gly Pro
        370                 375                 380
Leu Gly Asp Pro Arg Leu Leu Ile Gly Glu Pro Arg Gly Pro Met Ile
385                 390                 395                 400
Asp Gln Arg Gly Leu Pro Met Asp Gly Arg Gly Gly Arg Asp Ser Arg
                405                 410                 415
Ala Met Glu Thr Arg Ala Met Glu Thr Glu Val Leu Glu Thr Arg Val
                420                 425                 430
Met Glu Arg Arg Gly Met Glu Thr Cys Ala Met Glu Thr Arg Gly Met
            435                 440                 445
Glu Ala Arg Gly Met Asp Ala Arg Gly Leu Glu Met Arg Gly Pro Val
        450                 455                 460
Pro Ser Ser Arg Gly Pro Met Thr Gly Gly Ile Gln Gly Pro Gly Pro
465                 470                 475                 480
Ile Asn Ile Gly Ala Gly Gly Pro Pro Gln Gly Pro Arg Gln Val Pro
                485                 490                 495
Gly Ile Ser Gly Val Gly Asn Pro Gly Ala Gly Met Gln Gly Thr Gly
                500                 505                 510
Ile Gln Gly Thr Gly Met Gln Gly Ala Gly Ile Gln Gly Gly Gly Met
            515                 520                 525
Gln Gly Ala Gly Ile Gln Gly Val Ser Ile Gln Gly Gly Gly Ile Gln
        530                 535                 540
Gly Gly Gly Ile Gln Gly Ala Ser Lys Gln Gly Gly Ser Gln Pro Ser
545                 550                 555                 560
Ser Phe Ser Pro Gly Gln Ser Gln Val Thr Pro Gln Asp Gln Glu Lys
                565                 570                 575
Ala Ala Leu Ile Met Gln Val Leu Gln Leu Thr Ala Asp Gln Ile Ala
            580                 585                 590
Met Leu Pro Pro Glu Gln Arg Gln Ser Ile Leu Ile Leu Lys Glu Gln
        595                 600                 605
Ile Gln Lys Ser Thr Gly Ala Ser
        610                 615
```

Also suitable as a nucleic acid molecule of the present invention is a nucleic acid molecule which hybridizes to at least 20 nucleotides of the nucleic acid molecule having a nucleotide sequence of SEQ ID NO: 1 under stringent conditions characterized by hybridization buffer comprising 5×SSC at a temperature of 54° C. For the purposes of defining the level of stringency, reference can conveniently be made to Sambrook et al., "Molecular Cloning: a Laboratory Manual, $2^{nd}$ Edition, Cold Spring Harbor, N.Y., Cold Spring Harbor Laboratory Press, at 11.45 (1989), which is hereby incorporated by reference in its entirety. Depending on the source and concentration of the nucleic acid involved in the hybridization, alternative conditions of stringency may be employed such as medium stringent conditions, which includes 1–4×SSC/0.25% w/v SDS at ≧45° C. for 2–3 hours. Another example of suitable high stringency conditions includes 0.1–1×SSC/0.1% w/v SDS at 60° C. for 1–3 hours. The skilled artisan is aware of various parameters which may be altered during hybridization and washing and that will either maintain or change the stringency conditions. For example, another stringent hybridization condition is hybridization at 4×SSC at 65° C., followed by a washing in 0.1×SSC at 65° C. for about one hour. Alternatively, an exemplary stringent hybridization condition is in 50% formamide, 4×SSC, at 42° C. Still another example of stringent conditions include hybridization at 62° C. in 6×SSC, 0.05× BLOTTO, and washing at 2×SSC, 0.1% SDS at 62° C.

Another aspect of the present invention is an isolated mouse nucleic acid molecule encoding a protein or polypeptide which controls RNA polyadenylation. The nucleic acid molecule is a variant of a somatic nucleic acid molecule and is functional when the somatic nucleic acid molecule is not functional. One form of the nucleic acid molecule of the present invention, identified herein as Cstf2, is isolated from a mouse cell, and has a nucleotide sequence of SEQ ID NO: 3 as follows:

```
gaattcggca cgaggtggtt cgccagagga cgacccttag acgaattcaa tctccgctgt 60
cctctcggca gcaatcatgt cgagtttggc ggtcagagac ccagccatgg atcgatcgct 120
gcgttcggtg ttcgtgggga acattccgta tgaggcgacg gaggagcagt taaaggacat 180
tttctcagag gttggttcag ttgtcagttt ccgtctcgtc tacgatagag agactgggaa 240
gcccaagggt tatggcttct gcgagtacca agaccaggag actgcgctca gtgccatgcg 300
aaacctcaat gggcgagagt ttagtgggag agcgcttcgg gtggacaatg ccgccagcga 360
aaagaacaag gaggagttaa agagcttagg cccggcggcc cccatcattg actcccccta 420
tggggaccct atcgacccag aagatgctcc agaatcgatt actagagcag tcgccagctt 480
gcccccagag cagatgtttg agctcatgaa gcagatgaag ttgtgtgtcc agaacagtca 540
ccaggaagct cgaaacatgc tacttcagaa cccacagttg gcgtatgctt tgctgcaggc 600
acaagtggtg atgagaatca tggatccaga gattgcactg aaaattttgc atcgtaagat 660
acatgtcaca ccactgatcc caggcaaatc tcagccggtc tctgggcctg gcctggtggg 720
ctgggctagt gggctggcgg ctggcccggc ccctgcccct ggcctctgcc cgggacctaa 780
cgtcatgttg aaccaacaga atcctcctgc ccctcagcct cagcatctgc caagaagacc 840
tgtgaaggac attccacctc tgatgcagac ctctatccag ggaggaattc cagctccggg 900
gccaatacca gctgcagttc ctggacctgg acctggttcc ttaactccag gaggagcaat 960
gcagccacaa gttggcatgc cagtggttgg tccagtgccc ctggagcgag acagatgca 1020
gatatcagat cctagacctc cgatgcctcg tggacccatg ccttctggtg gcatacctcc 1080
tcgaggacta ctgggagatg ctccaaatga cccacgtgga gggactttgc tctcagtgac 1140
tggagaagta gagcccaggg gctatatggg accacccat cagggtcctc caatgcatca 1200
tggtcatgac aaccgtgcc ctgcctcaca tgatatgaga ggaggaccat tggcagcaga 1260
tcccagaatg ctaattggag agcccagagg tcccatgata gatcagagag gtctacctat 1320
ggatggtaga ggaggtagag aatctcgagg gatggagact cggcccatgg aaactgaggt 1380
cttggagcca cgaggaatgg agagaaggat ggagacctgc gcgatggaaa ccagaggcat 1440
ggatgcaaga ggactagaga tgagggcccc tggccctagt tccagaggtc cgatgactgg 1500
tggaatccag ggtcctggcc ctattaatat ggggcaggt ggccctcagg gacctagaca 1560
ggttccaaat attgcaggag tgggaaatcc tggaggtacc atgcaggggg caggtataca 1620
aggaggaggg atgcagggag caggtatgca aggaggaggg atgcaaggag caggcatgca 1680
aggaggaggg atgcagggag ctggcatgca agcagggatg cagggagcta gcatgcaagg 1740
agggatgcag ggagctggca tgcaaggagc cagtaagcaa ggtggaggcc agcctagcag 1800
ttttagccct gggcaaagcc aggtaactcc acaagatcaa gaaaaagcag ctttgatcat 1860
gcaggttctc cagctgactg cggatcagat tgccatgctg cctcccgaac aaaggcagag 1920
catttgatt ttaaaggaac aaatccagaa atccactggg gcttcttgaa tggttttcaa 1980
ctaagaagca cttagttact ccttcagagt ttattctgtg gcatgaagtg gtgcaaaaag 2040
```

-continued

```
ctgtcttctg tgttcgcaca ctttaaccat ttaaggtttc cttctcccta gatcttaatc  2100
tttcttctag tcctgtcact ttctgcttcc cttttagctt tttgatggag gttatggagt  2160
ggaaggagtg ggcctgttca ctttgtcact gttactctac cacgtaccct gaaaataact  2220
acatcatcca ccaagtaagg ctatgaggaa gatgcaggag gaataacatg tctgcacttt  2280
gttaactgcg tctttaaaaa tcccgagtaa gctgggaact acataaaaat tgaaagtgac  2340
ttgttacagt attgatatac taagatggtt taaaggtttt tggttgtata ttaactgaat  2400
gtcagcatct taagatacac ttttttggtaa accaaaatac tgtagagtaa taagattaat  2460
gtttagttat tttggaatta ttttgaaata ttggagctaa cagtctgtgg tgtagatgta  2520
gggttttttt tgttttttgtt tttttttttt taagcattgt tatctgtaaa aaggtaattt  2580
tcatttacct gactttttg agacaactaa tattcttgcc tggtcccacc tggtgatttt  2640
gcagaatagt tgtagtgtca gctgaattat ataaagccgc ctctgaggag actcaagtga  2700
tttcctaata catttctcta aaaaaattct taagcaccaa gtctggttgt aagtagtttt  2760
ttcatgtcat ctgaaaatag cagttagaca tggggtcgga ctttcttgag taatggaggg  2820
tttttcagta aagctcccac ccaggttctt gataaaccac tatccatacg cagatggaat  2880
ccatttggtc agcaggaatc agaagttaaa aaatcttagt cttcgaattt tgacgtgtct  2940
tacagtttga taactttcac aaagtacttt cctgccatca gcttaactag aactgaggcc  3000
caagtgatct gacagctctg ctcaacttag tattttatttt cttagaactc tcaagagcca  3060
tttggtcata acatacattc ctatcagatg tgttttaaaa taaggagtgt ggaatttaat  3120
acatttcctt tagagctacc atactatttt ttgacattaa gtgtgtggca cctagacacc  3180
atgtcatatc tagttaatga gcagaaacaa gcacaagttc ccacttgacc aagtgatagt  3240
cctctgtagg aaactaacta cccagctaca gagggaagag tagccttagg gagagagctg  3300
acccaagggt ctactttgtc cttggaaagt ttgagcattt tcagtgtaca gagttttcat  3360
tcctaggcta ttttccatcg acttagtttt ttgtgctagt gttaaactct ctgtggtttc  3420
ctctgcttct cctttgctga agttggtttg tgttttgtac ttttgtgcta gttctggcta  3480
attccaattg cttgctttcg aaattgcggt tgctagccca aaacttctta tagtctttgt  3540
tataagaaaa tctctgcatt gtttaatgaa aattaaataa aaaggttgta taattaaaaa  3600
aaaaaaaaaa a                                                      3611
```

The nucleic acid sequence corresponding to SEQ ID NO: 3 encodes a variant of murine CstF-64, identified herein as mτCstF-64, having a deduced amino acid sequence corresponding to SEQ ID NO: 4, as follows:

```
Met Ser Ser Leu Ala Val Arg Asp Pro Ala Met Asp Arg Ser Leu Arg
  1               5                  10                  15

Ser Val Phe Val Gly Asn Ile Pro Tyr Glu Ala Thr Glu Glu Gln Leu
                 20                  25                  30

Lys Asp Ile Phe Ser Glu Val Gly Ser Val Val Ser Phe Arg Leu Val
             35                  40                  45

Tyr Asp Arg Gln Thr Gly Lys Pro Lys Gly Tyr Gly Phe Cys Glu Tyr
         50                  55                  60

Gln Asp Gln Glu Thr Ala Leu Ser Ala Met Arg Asn Leu Asn Gly Arg
 65                  70                  75                  80

Gln Phe Ser Gly Arg Ala Leu Arg Val Asp Asn Ala Ala Ser Glu Lys
                 85                  90                  95

Asn Lys Glu Glu Leu Lys Ser Leu Gly Pro Ala Ala Pro Ile Ile Asp
```

-continued

```
                100                 105                 110
Ser Pro Tyr Gly Asp Pro Ile Asp Pro Glu Asp Ala Pro Gln Ser Ile
            115                 120                 125
Thr Arg Ala Val Ala Ser Leu Pro Pro Gln Gln Met Phe Gln Leu Met
130                 135                 140
Lys Gln Met Lys Leu Cys Val Gln Asn Ser His Gln Glu Ala Arg Asn
145                 150                 155                 160
Met Leu Leu Gln Asn Pro Gln Leu Ala Tyr Ala Leu Leu Gln Ala Gln
                165                 170                 175
Val Val Met Arg Ile Met Asp Pro Glu Ile Ala Leu Lys Ile Leu His
                180                 185                 190
Arg Lys Ile His Val Thr Pro Leu Ile Pro Gly Lys Ser Gln Pro Val
            195                 200                 205
Ser Gly Pro Gly Leu Val Gly Trp Ala Ser Gly Leu Ala Ala Gly Pro
    210                 215                 220
Ala Pro Ala Pro Gly Leu Cys Pro Gly Pro Asn Val Met Leu Asn Gln
225                 230                 235                 240
Gln Asn Pro Pro Ala Pro Gln Pro Gln His Leu Pro Arg Arg Pro Val
                245                 250                 255
Lys Asp Ile Pro Pro Leu Met Gln Thr Ser Ile Gln Gly Gly Ile Pro
                260                 265                 270
Ala Pro Gly Pro Ile Pro Ala Ala Val Pro Gly Pro Gly Pro Gly Ser
            275                 280                 285
Leu Thr Pro Gly Gly Ala Met Gln Pro Gln Val Gly Met Pro Val Val
    290                 295                 300
Gly Pro Val Pro Leu Glu Arg Gly Gln Met Gln Ile Ser Asp Pro Arg
305                 310                 315                 320
Pro Pro Met Pro Arg Gly Pro Met Pro Ser Gly Ile Pro Pro Arg
                325                 330                 335
Gly Leu Leu Gly Asp Ala Pro Asn Asp Pro Arg Gly Gly Thr Leu Leu
            340                 345                 350
Ser Val Thr Gly Gln Val Gln Pro Arg Gly Tyr Met Gly Pro Pro His
    355                 360                 365
Gln Gly Pro Pro Met His His Gly His Asp Asn Arg Gly Pro Ala Ser
370                 375                 380
His Asp Met Arg Gly Gly Pro Leu Ala Ala Asp Pro Arg Met Leu Ile
385                 390                 395                 400
Gly Glu Pro Arg Gly Pro Met Ile Asp Gln Arg Gly Leu Pro Met Asp
                405                 410                 415
Gly Arg Gly Gly Arg Glu Ser Arg Gly Met Glu Thr Arg Pro Met Gln
            420                 425                 430
Thr Glu Val Leu Glu Pro Arg Gly Met Glu Arg Arg Met Glu Thr Cys
    435                 440                 445
Ala Met Gln Thr Arg Gly Met Asp Ala Arg Gly Leu Gln Met Arg Gly
            450                 455                 460
Pro Gly Pro Ser Ser Arg Gly Pro Met Thr Gly Gly Ile Gln Gly Pro
465                 470                 475                 480
Gly Pro Ile Asn Met Gly Ala Gly Pro Gln Gly Pro Arg Gln Val
                485                 490                 495
Pro Asn Ile Ala Gly Val Gly Asn Pro Gly Gly Thr Met Gln Gly Ala
            500                 505                 510
Gly Ile Gln Gly Gly Gly Met Gln Gly Ala Gly Met Gln Gly Gly Gly
    515                 520                 525
```

```
                          -continued
Met Gln Gly Ala Gly Met Gln Gly Gly Gly Met Gln Gly Ala Gly Met
    530                 535             540

Gln Ala Gly Met Gln Gly Ala Ser Met Gln Gly Gly Met Gln Gly Ala
545             550             555                 560

Gly Met Gln Gly Ala Ser Lys Gln Gly Gly Gly Gln Pro Ser Ser Phe
                565             570                 575

Ser Pro Gly Gln Ser Gln Val Thr Pro Gln Asp Gln Glu Lys Ala Ala
            580             585             590

Leu Ile Met Gln Val Leu Gln Leu Thr Ala Asp Gln Ile Ala Met Leu
        595             600             605

Pro Pro Glu Gln Arg Gln Ser Ile Leu Ile Leu Lys Glu Gln Ile Gln
        610             615             620

Lys Ser Thr Gly Ala Ser
625             630
```

The human τCstF-64 cDNA is largely similar to that of mouse (showing 89.8% similarity): τCstF-64 in both species shares the two insert regions, a single amino acid difference in the RNA-binding domain, and the CstF-77-interaction domain. The gene for human τCstF-64, CSTF2T is on chromosome 10q22–23, which is homologous with Cstf2t on mouse chromosome 19. Furthermore, the protein encoded by human τCstF-64 was recognized by the 6A9 monoclonal antibody (Wallace et al., "Two Distinct Forms of the 64,000 $M_r$ Protein of the Cleavage Stimulation Factor are Expressed in Mouse Male Germ Cells," *Proc. Natl. Acad. Sci. USA* 96:6763–6768 (1999), which is hereby incorporated by reference in its entirety) that is diagnostic for τCstF-64 (Dass et al., "The Gene for a Variant Form of the Polyadenylation Protein CstF-64 is on Chromosome 19 and is Expressed in Pachytene Spermatocytes in Mice," *J. Biol. Chem.* 276:8044–8050 (2001), which is hereby incorporated by reference in its entirety). Based on this evidence, it is proposed that CSTF2T is the human ortholog of mouse Cstf2t, and that likely it is expressed in human germ cells as was described in mouse (Wallace et al., "Two Distinct Forms of the 64,000 $M_r$ Protein of the Cleavage Stimulation Factor are Expressed in Mouse Male Germ Cells," *Proc. Natl. Acad. Sci. USA* 96:6763–6768 (1999), which is hereby incorporated by reference in its entirety) and rat. Interestingly, there has been one report of human male infertility associated with a lesion of chromosome 10q22–23 (Bourrouillou et al., "Anomalies Chromosomiques Chez les Hommes Steriles, Etude Chez 241 Sujets. [Chromosome Aberrations in Sterile Males. Study of 241 Cases (Letter)]," *Nouv Presse Med* 7:3777 (1978), which is hereby incorporated by reference in its entirety), which suggests an essential role for τCstF-64 in human fertility.

Another aspect of the present invention is a nucleic acid construct including a nucleic acid molecule of the present invention encoding a protein or polypeptide which controls RNA polyadenylation. This involves incorporating any nucleic acid molecule of the present invention into host cells using conventional recombinant DNA technology. The introduction of a gene into a host is facilitated by first introducing the gene sequence into a suitable nucleic acid vector. "Vector" is used herein to mean any genetic element, such as a plasmid, phage, transposon, cosmid, chromosome, virus, virion, etc., which is capable of replication when associated with the proper control elements, and which is capable of transferring gene sequences between cells. Thus, the term includes cloning and expression vectors, as well as viral vectors, including adenoviral and retroviral vectors.

Exemplary vectors include, without limitation, the following: lambda vector system gt11, gt WES.tB, Charon 4, and plasmid vectors such as pBR322, pBR325, pACYC177, pACYC184, pUC8, pUC9, pUC18, pUC19, pLG339, pR290, pKC37, pKC101, SV 40, pBluescript II SK +/− or KS +/− (see "Stratagene Cloning Systems" Catalog (1993) from Stratagene, La Jolla, Calif., which is hereby incorporated by reference in its entirety), pQE, pIH821, pGEX, pET series (see F. W. Studier et. al., "Use of T7 RNA Polymerase to Direct Expression of Cloned Genes," *Gene Expression Technology* Vol. 185 (1990), which is hereby incorporated by reference in its entirety), and any derivatives thereof.

The nucleic acid molecules of the present invention may be inserted into any of the many available expression vectors and cell systems using reagents that are well known in the art. U.S. Pat. No. 4,237,224 to Cohen and Boyer, which is hereby incorporated by reference in its entirety, describes the production of expression systems in the form of recombinant plasmid vectors using restriction enzyme cleavage and ligation with DNA ligase.

A variety of host-vector systems may be utilized to express the protein-encoding sequence of the present invention. Primarily, the vector system must be compatible with the host cell used. Host-vector systems include but are not limited to the following: bacteria transformed with bacteriophage DNA, plasmid DNA, or cosmid DNA; microorganisms such as yeast containing yeast vectors; mammalian cell systems infected with virus (e.g., vaccinia virus, adenovirus, retrovirus, etc.); insect cell systems infected with virus (e.g., baculovirus); and plant cells infected by bacteria. The expression elements of these vectors vary in their strength and specificities. Depending upon the host-vector system utilized, any one of a number of suitable transcription and translation elements can be used.

Transcription of DNA is dependent upon the presence of a promoter, which is a DNA sequence that directs the binding of RNA polymerase and thereby promotes mRNA synthesis. The DNA sequences of eukaryotic promoters differ from those of prokaryotic promoters. Furthermore, eukaryotic promoters and accompanying genetic signals may not be recognized in, or may not function in, a prokaryotic system, and, further, prokaryotic promoters are not recognized and do not function in eukaryotic cells.

Promoters vary in their "strength" (i.e., their ability to promote transcription). For the purposes of expressing a cloned gene, it is desirable to use strong promoters in order to obtain a high level of transcription and, hence, expression of the gene. Depending upon the host cell system utilized, any one of a number of suitable promoters may be used. For instance, when cloning in *E. coli*, its bacteriophages, or plasmids, promoters such as the T7 phage promoter, lac promoter, trp promoter, recA promoter, ribosomal RNA promoter, the $P_R$ and $P_L$ promoters of coliphage lambda and others, including but not limited, to lacUV5, ompF, bla, lpp, and the like, may be used to direct high levels of transcription of adjacent DNA segments. Additionally, a hybrid trp-lacUV5 (tac) promoter or other *E. coli* promoters produced by recombinant DNA or other synthetic DNA techniques may be used to provide for transcription of the inserted gene.

Common promoters suitable for directing expression in mammalian cells include, without limitation, β-globin, β-actin, actin, Cstf2t, SV40, MMTV, metallothionein-1, adenovirus Ela, CMV, immediate early, immunoglobulin heavy chain promoter and enhancer, and RSV-LTR.

Similarly, translation of mRNA in prokaryotes depends upon the presence of the proper prokaryotic signals which differ from those of eukaryotes. Efficient translation of mRNA in prokaryotes requires a ribosome binding site called the Shine-Dalgarno ("SD") sequence on the mRNA. This sequence is a short nucleotide sequence of mRNA that is located before the start codon, usually AUG, which encodes the amino-terminal methionine of the protein. The SD sequences are complementary to the 3'-end of the 16S rRNA (ribosomal RNA) and probably promote binding of mRNA to ribosomes by duplexing with the rRNA to allow correct positioning of the ribosome. For a review on maximizing gene expression see Roberts et al., "Maximizing Gene Expression on a Plasmid Using Recombination In vitro," *Methods in Enzymology* 68:473 (1979), which is hereby incorporated by reference in its entirety.

All of the nucleic acid constructs of the present invention also include operable 3' regulatory elements, selected from among those elements which are capable of providing correct transcriptional termination and proper polyadenylation of mRNA for expression in the host cell of choice, operably linked to a DNA molecule which encodes a protein of choice. Exemplary 3' regulatory elements include, without limitation, the nopaline synthase ("nos") 3' regulatory region (Fraley, et al., "Expression of Bacterial Genes in Plant Cells," *Proc. Nat'l Acad. Sci. USA* 80(15):4803–4807 (1983), which is hereby incorporated by reference in its entirety) and the cauliflower mosaic virus ("CaMV") 3' regulatory region (Odell, et al., "Identification of DNA Sequences Required for Activity of the Cauliflower Mosaic Virus 35S Promoter," *Nature* 313(6005):810–812 (1985), which is hereby incorporated by reference in its entirety). An example of a commonly-used 3' regulatory element for expression of genes of interest in mammalian cells is the SV40 polyadenylation signal derived from the SV40 virus. Virtually any 3' regulatory element known to be operable in the host cell of choice will suffice for proper expression of the genes contained in the plasmids of the present invention.

Bacterial host cell strains and expression vectors may be chosen which inhibit the action of the promoter unless specifically induced. In certain operons, the addition of specific inducers is necessary for efficient transcription of the inserted DNA. For example, the lac operon is induced by the addition of lactose or IPTG (isopropylthio-beta-D-galactoside). A variety of other operons, such as trp, pro, etc., are under different controls.

Preferably, transformed cells are first identified using a selection marker simultaneously introduced into the host cells along with the nucleic acid construct of the present invention. Suitable selection markers include, without limitation, markers encoding for antibiotic resistance, such as the nptII gene which confers kanamycin resistance (Fraley, et al., *Proc. Natl. Acad. Sci. USA* 80:4803–4807 (1983), which is hereby incorporated by reference in its entirety), and the genes which confer resistance to gentamycin, G418, hygromycin, streptomycin, spectinomycin, tetracycline, chloramphenicol, and the like. Cells or tissues are grown on a selection medium containing the appropriate antibiotic, whereby generally only those transformants expressing the antibiotic resistance marker continue to grow. In one embodiment of the present invention, the nucleic acid construct of the present invention also includes one or more nucleic acid molecules encoding for a reporter gene. A reporter gene encodes a detectable protein, allowing for identification and localization of transgene expression in a host. Reporter proteins suitable for this aspect of the present invention include, without limitation, chloramphenicol acetyltransferase ("CAT"), luciferase, LacZ, green fluorescent protein ("GFP") (Chalfie et al., "Green Fluorescent Protein as a Marker for Gene Expression," *Science* 263 (5148):802–805 (1994); Heim et al., "Wavelength Mutations and Posttranslational Autooxidation of Green Fluorescent Protein," *Proc. Natl. Acad. Sci. USA* 91:12501–12504 (1994) which are hereby incorporated by reference in their entirety), and β-glucuronidase ("GUS")(Jefferson et al., "GUS Fusions: β Glucuronidase as a Sensitive and Versatile Gene Fusion Marker in Higher Plants," *EMBO J.* 6:3901–3907 (1987), which is hereby incorporated by reference in its entirety). The selection marker employed will depend on the target species; for certain target species, different antibiotics, or biosynthesis selection markers are preferred.

The nucleic acid molecule of the present invention, appropriate transcriptional and translational regulatory elements as described above, and any additional desired components, including, without limitation, enhancers, leader sequences, markers, etc., are cloned into the vector of choice using standard cloning procedures in the art, such as described in Sambrook et al., *Molecular Cloning: A Laboratory Manual*, Cold Spring Laboratory, Cold Spring Harbor, N.Y. (1989), Ausubel et al., "Short Protocols in Molecular Biology," New York:Wiley (1999), and U.S. Pat. No. 4,237,224 to Cohen and Boyer, which are hereby incorporated by reference in their entirety.

Once the nucleic acid construct containing the nucleic acid molecule of the present invention has been cloned into an expression system, it is ready to be incorporated into a host cell by means of transformation and replicated in unicellular cultures including prokaryotic organisms and eukaryotic cells grown in tissue culture. Accordingly, another aspect of the present invention relates to a method of making a recombinant cell having a nucleic construct including a nucleic acid molecule of the present invention encoding a protein or polypeptide for polyadenylation. Basically, this method is carried out by transforming a host cell with the vector containing the nucleic acid construct of the present invention under conditions effective to yield transcription of the nucleic acid molecule in the host cell. Preferably, the nucleic acid construct of the present invention is stably inserted into the genome of the recombinant host cell as a result of the transformation, although transient may be suitable in some aspects.

Such incorporation can be carried out by various forms of transformation, depending upon the vector/host cell system. Recombinant molecules can be introduced into cells via transformation, particularly transduction, conjugation, mobilization, or electroporation. The nucleic acid sequences are cloned into the host cell using standard cloning procedures known in the art, as described by Sambrook et al., *Molecular Cloning: A Laboratory Manual*, Second Edition, Cold Spring Laboratory, Cold Spring Harbor, N.Y. (1989), which is hereby incorporated by reference in its entirety. Suitable host cells include, but are not limited to, bacteria, virus, yeast, mammalian cells, including mouse and human, and the like.

Transient expression in protoplasts allows quantitative studies of gene expression since the population of cells is very high (on the order of $10^6$). To deliver nucleic acid inside protoplasts, several methodologies have been proposed, but the most common are electroporation (Neumann et al., "Gene Transfer into Mouse Lyoma Cells by Electroporation in High Electric Fields," *EMBO J.* 1: 841–45 (1982); Wong et al., "Electric Field Mediated Gene Transfer," *Biochem Biophys Res Commun* 30;107(2):584–7 (1982); Potter et al., "Enhancer-Dependent Expression of Human Kappa Immunoglobulin Genes Introduced into Mouse pre-B Lymphocytes by Electroporation," *Proc. Natl. Acad. Sci. USA* 81: 7161–65 (1984), which are hereby incorporated by reference in their entirety) and polyethylene glycol (PEG) mediated DNA uptake, Sambrook et al., *Molecular Cloning: A Laboratory Manual*, Chap. 16, 2d Edition, Cold Spring Laboratory, Cold Spring Harbor, N.Y. (1989), which is hereby incorporated by reference in its entirety). During electroporation, the nucleic acid is introduced into the cell by means of a reversible change in the permeability of the cell membrane due to exposure to an electric field. PEG transformation introduces the nucleic acid by changing the elasticity of the membranes. Unlike electroporation, PEG transformation does not require any special equipment. Another appropriate method of introducing the gene construct of the present invention into a host cell is fusion of protoplasts with other entities, either minicells, cells, lysosomes, or other fusible lipid-surfaced bodies that contain the chimeric gene (Fraley, et al., *Proc. Natl. Acad. Sci. USA*, 79:1859–63 (1982), which is hereby incorporated by reference in its entirety).

Another aspect of the present invention relates to a method of diagnosing male infertility in a subject. This involves providing a semen sample from a subject and testing the sample for a presence or absence of the protein or polypeptide of the present invention. The absence of the protein or polypeptide in the sample indicates infertility. This method may involve contacting a semen sample from a subject with an antibody or binding portion thereof, under conditions effective to permit formation of an antigen-antibody/binding portion complex. The formation of an antigen-antibody/binding portion complex is determined by using an assay system. Examples of an assay system suitable for the determination of the presence of a polyadenylation protein or polypeptide of the present invention by detection of an antigen-antibody/binding portion complex include, without limitation, an enzyme-linked immunosorbent assay, a radioimmunoassay, a gel diffusion precipitin reaction assay, an immunodiffusion assay, an agglutination assay, a fluorescent immunoassay, a protein A immunoassay, and an immunoelectrophoresis assay. Conditions suitable for formation of the antigen-antibody/binding portion complex will dictated by the choice of assay system, and are known or can be readily determined by those skilled in the art. For the purposes of this application, infertility is defined broadly as any one of a number of male conditions that can lead to either subfertility or infertility in accordance with the latest National Institutes of Child Health and Human Development guidelines, which can be found the website for the National Institutes for Health, USA (which is hereby incorporated by reference in its entirety). These conditions include decreased sperm count ("oligospermia") and total absence of sperm in the ejaculate ("azoospermia"). Decreased sperm count (fewer than 20,000,000 sperm per milliliter of ejaculate) can be further associated with abnormal spermatozoa ("teratozoospermia") or reduced sperm motility ("asthenozoospermia"). Additional discussion of male infertility can be found at Johnson, M. H. and Everitt, B. J., *Essential Reproduction*, Fourth Edition, Blackwell Science, Inc. Cambridge, Mass. pg. 250–251 (1995), which is hereby incorporated by reference in its entirety.

Suitable antibodies for this aspect of the present invention may be derived using methods known in the art, such as those described in *Monoclonal Antibodies—Production, Engineering and Clinical Applications*, Ritter et al., Eds. Cambridge University Press, Cambridge, UK (1995); Milstein and Kohler, *Eur. J. Immunol.* 6:511 (1976); Kohler and Milstein, *Nature*, 256:495 (1975); Milstein and Kohler, *Eur. J. Immunol.*, 6:511 (1976); Harlow, et. al., Eds., *Antibodies: A Laboratory Manual*, Cold Spring Harbor Laboratory, N.Y. (1988); J. Goding, *Monoclonal Antibodies: Principles and Practice*, (pp. 98–118) Academic Press: New York (1983), which are hereby incorporated by reference in their entirety. Also suitable in this aspect of the present invention are antibodies previously described for CstF-64 (Wallace et al., "Two Distinct Forms of the 64,000 $M_r$ Protein of the Cleavage Stimulation Factor are Expressed in Mouse Male Germ Cells," *Proc. Natl. Acad. Sci. USA* 96:6763–6768 (1999), which is hereby incorporated by reference in its entirety), including that known as "6A9," which is described in greater detail in the Examples, below. This method may, alternatively, involve any other method of protein detection and identification known in the art and suitable for use with the protein or polypeptide of the present invention.

The present invention also relates to a second method of detecting infertility in a male subject. This method involves providing a semen sample from a subject and determining a presence or absence in the sample of the subject nucleic acid molecule according to claim 1, where the absence of the nucleic acid molecule indicates infertility. The presence or absence of the nucleic acid molecule of the present invention can be determined using any method that is capable of determining the presence, or lack thereof, of the nucleic acid molecule, or a portion thereof. Such determinations can be made, for example, by direct sequencing of the sample for the nucleic acid of the present invention using primers designed to recognize a portion of the nucleic acid sequence of the present invention; or by Southern blot, polymerase chain reaction, ligase chain reaction, or using standard procedures in the art, such as described in Sambrook et al., *Molecular Cloning: A Laboratory Manual*, Cold Spring Laboratory, Cold Spring Harbor, N.Y. (1989), and Ausubel et al., "Short Protocols in Molecular Biology," New York: Wiley (1999), which are hereby incorporated by reference in their entirety.

The present invention also relates to third method of diagnosing male infertility. In this aspect, infertility may be related to an auto-immune disease condition. This method may relate to the situation where a subject suffers from a disease condition that causes the body to generate antibodies to naturally-occurring proteins, therefore, the subject generates antibodies to his own hτCstF-64 protein. This method involves providing a semen sample from a subject and contacting the sample with the protein or polypeptide of the present invention, and detecting a presence in the semen sample of antibody to the protein or polypeptide of the present invention. The presence of an antibody to the protein or polypeptide indicates the infertility of the subject. In this method, the protein or polypeptide of the present invention, or a fragment thereof, is used to contact the semen sample under conditions to allow the formation of an antigen/antibody complex, thereby indicating that the subject is producing antibodies to hτCstF-64 (Calamera, et al., "Male Antisperm Antibodies: Association With a Modified Sperm Stress Test and Lipid Peroxidation," *Andrologia* 34, 63–68 (2002);Chiu et al., "Use of Antisperm Antibodies in Differential Display Western Blotting to Identify Sperm Proteins Important in Fertility," *Human Reproduction* 17(4):984–989 (2002), which are hereby incorporated by reference in their entirety). In one embodiment, the antibody detected is an anti-idiopathic antibody The formation of an antigen-antibody/binding portion complex is determined by using an assay system, as described herein above, and the presence of antibody indicates infertility of the subject (Calamera, et al., "Male Antisperm Antibodies: Association With a Modified Sperm Stress Test and Lipid Peroxidation," *Andrologia* 34, 63–68 (2002);Chiu et al., "Use of Antisperm Antibodies in Differential Display Western Blotting to Identify Sperm Proteins Important in Fertility," *Human Reproduction* 17(4):984–989 (2002), which are hereby incorporated by reference in their entirety). Conditions suitable for formation of the antigen-antibody/binding portion complex will be dictated by the choice of assay system, and are known or can be readily determined by those skilled in the art.

Another aspect of the present invention is a method of relates to a method for diagnosing a cancerous condition in a subject. This involves providing a biological sample from a subject and testing the biological sample for the presence of antibody to the protein or polypeptide of the present invention, wherein the presence of the antibody indicates a cancerous condition in the subject. Without being bound to a theory, a subject suffering from a cancerous condition may begin to produce antibodies to some of their own naturally-occurring proteins (see e.g., Boman et al., "Newly Diagnosed Bladder Cancer: the Relationship of Initial Symptoms, Degree of Microhematuria and Tumor Marker Status," *J. Urology* 168(5):1955–1959 (2002), which is hereby incorporated by reference in its entirety). This category of disease has given rise to a field of therapy based on DNA vaccines (Schadendorf D., "Gene-Based Therapy of Malignant Melanoma," *Seminars in Oncology* 29(5):503–512 (2002), which is hereby incorporated by reference in its entirety).

Another aspect of the present invention is a method of contraception for mammals. This involves introducing to a mammal a therapeutic agent capable of inactivating the protein or polypeptide of the present invention in the testis of the subject, under conditions effective to achieve contraception in the mammal. The protein or polypeptide which may be targeted in this aspect of the present is that having SEQ ID NO: 2, or a fragment thereof. Any mammal may be the subject of this aspect of the present invention, including, but not limited to a human subject.

EXAMPLES

Example 1

Antibody Interaction Mapping

Full-length cDNA encoding human CstF-64 (Takagaki et al., "The Human 64-kDa Polyadenylation Factor Contains a Ribonucleoprotein-type RNA Binding Domain and Unusual Auxiliary Motifs," *Proc. Natl. Acad. Sci. USA* 89(4):1403–1407 (1992), which is hereby incorporated by reference in its entirety) was cloned in-frame into the pGEX2T vector (Amersham Pharmacia Biotech, Piscataway, N.J.). 3' end truncations were made by limited enzymatic digestion of the above construct to obtain versions that terminated at amino acids 531, 425, and 325. A fourth construct was made by introducing a 290-bp BamHI fragment of CstF-64 encoding amino acids 316–412 into pGEX2T. Constructs were introduced into *Escherichia coli* DH5α cells by transformation, grown to mid-logarithmic phase, and induced for 3 h at 37° C. with 1 mM isopropyl β-D-thiogalactoside. Bacterial extracts were prepared in SDS-PAGE loading buffer by sonication and boiling and prepared for immunoblotting with either the 3A7 or 6A9 monoclonal antibody as described previously (Wallace et al., "Two Distinct Forms of the 64,000 Mr Protein of the Cleavage Stimulation Factor are Expressed in Mouse Male Germ Cells," *Proc. Natl. Acad. Sci. USA* 96:6763–6768 (1999), which is hereby incorporated by reference in its entirety).

Example 2

Complementary DNA Isolation

An adult mouse pachytene spermatocyte cDNA library in Uni-Zap XR vector (McCarrey et al., "Construction and Preliminary Characterization of a Series of Mouse and Rat Testis cDNA Libraries," *J. Androl.* 20(5):635–639 (1999), which is hereby incorporated by reference in its entirety) was screened using the 290-bp BamHI cDNA fragment of CstF-64 encoding amino acids 316–412. Filters were denatured in 0.5 m NaOH, 1.5 M NaCl, neutralized in 0.5 M Tris-HCl, pH 7.4, 1.5 M NaCl, and hybridized with $\alpha[^{32}P]$ dCTP-labeled cDNA probe in hybridization solution (10× SSC, 0.05 M sodium phosphate, pH 6.5, 5× Denhardt's solution, 0.1% $Na_4P_2O_7$, 0.5% SDS, 0.05 mg/ml salmon sperm DNA) overnight at 65° C., and exposed to film at −80° C. with an intensifying screen. Positive plaques were purified by two additional rounds of screening. Plasmid rescue into pBluescript SK-was according to the manufacturer's directions (Stratagene, La Jolla, Calif.). Of two million plaques screened initially, 24 hybridized to the probe, all of which represented the same mRNA transcript (see Example 9). The longest clone (3611 bp) was designated mτCstF-64 and was sequenced by a combination of primer walking and subcloning, using the Sequenase 2.0 kit (U.S. Biochemical Corp., Cleveland Ohio). Sequences were aligned and grouped into contigs using the SeqMan analysis program (DNA Star).

Example 3

In Vitro Transcription and Translation

Polypeptides corresponding to human (hCstF-64) (Takagaki et al., "The Human 64-kDa Polyadenylation Factor Contains a Ribonucleoprotein-type RNA Binding Domain and Unusual Auxiliary Motifs," *Proc. Natl. Acad. Sci. USA* 89(4):1403–1407 (1992), which is hereby incorporated by reference in its entirety)), mouse (mCstF-64) (Dass et al., "Overexpression of the CstF-64 and CPSF-160 Polyadenylation Protein Messenger RNAs in Mouse Male Germ Cells," *Biol. Reprod.* 64(6):1722–1729 (2001), which is hereby incorporated by reference in its entirety)), and the mouse τCstF-64 (mτCstF-64) cDNAs were prepared in vitro using the T3 TNT Coupled Reticulocyte Lysate System (Promega, Madison, Wis.). Products from the transcription/translation reactions were separated on a 10% SDS-PAGE and immunoblotted with either the 3A7 or 6A9 monoclonal antibody (Wallace et al., "Two Distinct Forms of the 64,000 Mr Protein of the Cleavage Stimulation Factor are Expressed in Mouse Male Germ Cells," *Proc. Natl. Acad. Sci. USA* 96:6763–6768 (1999), which is hereby incorporated by reference in its entirety).

Example 4

Peptide Mapping by Limited Proteolysis

Radiolabeled proteins corresponding to mCstF-64 and mτCstF-64 were made in vitro using the T3 TNT reticulocyte lysate system (Promega, Madison, Wis.) with [$^{35}$S] methionine (PerkinElmer Life Sciences, Foster City, Calif.). Translated products were separated on 10% SDS-PAGE, and the band corresponding to full-length to mτCstF-64 protein was excised and eluted overnight at 4° C. in Cleveland buffer (0.125 M Tris-HCl, pH 6.8, 0.5% SDS, 1% glycerol, 0.0001% bromphenol blue (Takagaki et al., "The Human 64-kDa Polyadenylation Factor Contains a Ribonucleoprotein-type RNA Binding Domain and Unusual Auxiliary Motifs," *Proc. Natl. Acad. Sci. USA* 89(4):1403–1407 (1992), which is hereby incorporated by reference in their entirety).

Radiolabeled τCstF-64 was made in vivo by incorporation of [$^{35}$S]methionine during short term culture of mouse seminiferous tubules. Testes from 8 CD-1 mice (Charles River Breeding Laboratories, Wilmington, Mass.) were decapsulated and washed several times in cold PBS to remove interstitial cells. Tubules were then washed in pre-warmed DMEM lacking methionine (Cellgro, Mediatech, Inc., Herndon, Va.) followed by incubation in DMEM containing 10 mM methionine, 2 mm glutamine, and 1.25 mCi/ml Tran-label (ICN, Irvine, Calif.) for 7 h at 32° C. (O'Brien, "Stage-Specific Protein Synthesis by Isolated Spermatogenic Cells Throughout Meiosis and Early Spermiogenesis in the Mouse," *Biol. Reprod.* 37(1):147–157 (1987), which is hereby incorporated by reference in its entirety). Following incubation, tubules were washed in DMEM, resuspended in RIPA (150 mM NaCl, 1% Nonidet P-40, 0.5% deoxycholate, 0.1% SDS, 50 mM Tris, pH 8.0), and sonicated on ice. After preclearing, samples were immunoprecipitated at 4° C. using the 6A9 monoclonal antibody and protein A-Sepharose beads as described (MacDonald et al., "The 64-Kilodalton Subunit of the CstF Polyadenylation Factor Binds to Pre-mRNAs Downstream of the Cleavage Site and Influences Cleavage Site Location," *Mol. Cell. Biol.* 14(10):6647–6654 (1994), which is hereby incorporated by reference in its entirety). Following immunoprecipitation, beads were washed in RIPA, boiled in Laemmli buffer (Laemmli, "Cleavage of Structural Proteins During the Assembly of the Head of Bacteriophage T4," *Nature* 227 (259):680–685 (1970), which is hereby incorporated by reference in its entirety), and digested with 0.1 or 1.0 μg of V8 protease (Sigma, St. Louis, Mo.) in the presence of 5 μg of bovine IgG protein (Bio-Rad Labs, Hercules, Calif.) for 30 min at 37° C. (Takagaki et al., "The Human 64-kDa Polyadenylation Factor Contains a Ribonucleoprotein-type RNA Binding Domain and Unusual Auxiliary Motifs," *Proc. Natl. Acad. Sci. USA* 89(4):1403–1407 (1992), Cleveland et al., "Peptide Mapping by Limited Proteolysis in Sodium Dodecyl Sulfate and Analysis by Gel Electrophoresis," *J. Biol. Chem.* 252(3):1102–1106 (1977), which are hereby incorporated by reference in their entirety). Polypeptide fragments were separated by 15% SDS-PAGE, followed by fluorography. The image was captured on x-ray film exposed in the presence of an intensifying screen at −80° C. The results are shown in FIG. 1. Lanes 1–3 were exposed to film for 10 days and lanes 4–6 were exposed for 105 days.

Example 5

Interspecific Mouse Backcross Mapping

Interspecific backcross progeny were generated by mating (C57BL/6J×*Mus spretus*) F1 females and C57BL/6J males as described (Wallace et al., "Two Distinct Forms of the 64,000 Mr Protein of the Cleavage Stimulation Factor are Expressed in Mouse Male Germ Cells," *Proc. Natl. Acad. Sci. USA* 96:6763–6768 (1999), Copeland et al., "Development and Applications of a Molecular Genetic Linkage Map of the Mouse Genome," *Trends Genet.* 7(4):113–118 (1991), which are hereby incorporated by reference in their entirety). A total of 205 N2 mice were used to map the Cstf2t locus. DNA isolation, restriction enzyme digestion, agarose gel electrophoresis, and Southern blot analysis were performed as described (Jenkins et al., "Organization, Distribution, and Stability of Endogenous Ecotropic Murine Leukemia Virus DNA Sequences in Chromosomes of *Mus musculus*," *J. Virol.* 43(1):26–36 (1982), which is hereby incorporated by reference). The probe, a 514-bp DraI/XhoI fragment of mτCstF-64 from the 3'-UTR, was labeled with α[$^{32}$P]dCTP using a nick translation primed labeling kit (Roche Molecular Biochemicals, Indianapolis, Ind.); washing was done to a final stringency of 0.8×SSCP (120 mM NaCl, 5 mM sodium citrate, 20 mM sodium phosphate, pH 6.8), 0.1% SDS at 65° C. A fragment of 0.5 kb was detected in TaqI-digested C57BL/6J DNA, and a fragment of 1.8 kb was detected in TaqI-digested *M. spretus* DNA. The presence or absence of the 1.8-kb TaqI *M. spretus*-specific fragment was followed in backcross mice. A description of the probes and RFLPs for the loci linked to Cstf2t including Gnaq and Fas has been reported previously (Watanabe-Fukunaga et al., "The cDNA Structure, Expression, and Chromosomal Assignment of the Mouse Fas antigen," *J. Immunol.* 148(4): 1274–1279 (1992), Wilkie et al., "Evolution of the Mammalian G Protein α Subunit Multigene Family," *Nat. Genet.* 1(2):85–91 (1992), which are hereby incorporated by reference in their entirety). Recombination distances were calculated using Map Manager, version 2.6.5 (Roswell Park Cancer Institute, Buffalo, N.Y.). Gene order was determined by minimizing the number of recombination events required to explain the allele distribution patterns.

Example 6

Recombinant Protein Purification

RNA-binding domains (RBDs) from human (hRBD) and mouse CstF-64 (mRBD) and mouse mτCstF-64 (mτRBD) were prepared as fusion polypeptides with N-terminal hexahistidine tags. Construction of the plasmid hRBD (formerly known as rHis64Δ247) was described previously (Takagaki et al., "The Human 64-kDa Polyadenylation Factor Contains a Ribonucleoprotein-type RNA Binding Domain and Unusual Auxiliary Motifs," *Proc. Natl. Acad. Sci. USA* 89(4):1403–1407 (1992), which are hereby incorporated by reference in their entirety). The RNA-binding domains of mCstF-64 (nucleotides 53–897) and mτCstF-64 (nucleotides 77–598) were cloned in frame with the hexahistidine tag of the pQE9 vector (Qiagen, Valencia, Calif.) to make mRBD and mτRBD, respectively. hRBD, mRBD, and mτRBD plasmid DNAs were transformed into UltraMAXDH5α-FT cells (Life Technologies, Inc., Gaithersburg, Md.), grown to mid-logarithmic phase, and induced at 37° C. for 3 h by the addition of isopropyl β-D-thiogalactoside to 1.5 mM. His-tagged recombinant proteins were isolated as described (Takagaki et al., "The Human 64-kDa Polyadenylation Factor Contains a Ribonucleoprotein-type RNA Binding Domain and Unusual Auxiliary Motifs," *Proc. Natl. Acad. Sci. USA* 89(4):1403–1407 (1992), which is hereby incorporated by reference in its entirety) and dialyzed against buffer D (20 mM HEPES, pH 7.9, 0.1 m KCl, 0.2 mm EDTA, 1.5 mm $MgCl_2$, 10% glycerol, 0.5 mM dithiothreitol, 0.5 mm phenylmethylsulfonyl fluoride (Dignam et al., "Accurate Transcription Initiation by RNA Polymerase II in a Soluble Extract from Isolated Mammalian Nuclei," *Nucleic Acids Res.* 11(5):1475–1489 (1983), which is hereby incorporated by reference in its entirety) overnight at 4° C. Recombinant proteins were quantified by comparison to bovine serum albumin standards after staining of 12.5% SDS-PAGE gels with Coomassie Brilliant Blue R-250.

Example 7

UV Cross-Linking 0.3 μg each of hRBD, mRBD, mτRBD, or bovine IgG (Bio-Rad, Hercules, Calif.) was mixed with $^{32}$P-labeled SVL substrate ($3\times10^4$ cpm (Wilusz et al., "A 64 kd Nuclear Protein Binds to RNA Segments that Include the AAUAAA Polyadenylation Motif," *Cell* 52(2):221–228 (1988), which is hereby incorporated by reference in its entirety)) in buffer D for 30 min at 30° C. Reaction mixtures were exposed to $10^7$ μJ/cm$^2$ of ultraviolet light in a CL-1000 Ultraviolet Cross-linker (Ultraviolet Products, Upland, Calif.). Control reactions were processed without exposure to UV. Reaction mixtures were incubated with 10 units of RNaseONE (Promega, Madison, Wis.) at 37° C. for 15 min. SDS-PAGE loading buffer was added, the samples boiled, and RNA-cross-linked polypeptides were separated on 12.5% SDS-PAGE. The gel was stained with Coomassie Blue to ensure equal loading of the recombinant proteins, destained, dried, and subjected to autoradiography at −80° C. with an intensifying screen.

Example 8

Epitopes for the Monoclonal Antibodies 3A7 and 6A9 Map to Two Distinct Regions of CstF-64 cDNA The monoclonal antibodies 3A7 and 6A9, obtained by using human CstF purified from HeLa cells, can distinguish the somatic (3A7) and variant (6A9) forms of CstF-64 in mice (Wallace et al., "Two Distinct Forms of the 64,000 Mr Protein of the Cleavage Stimulation Factor are Expressed in Mouse Male Germ Cells," *Proc. Natl. Acad. Sci. USA* 96:6763–6768 (1999)). In human, however, both antibodies recognize the somatic form of CstF-64 (Takagaki et al., "A Multisubunit Factor, CstF, is Required for Polyadenylation of Mammalian Pre-mRNAs," *Genes Dev.* 4:2112–2120 (1990), which is hereby incorporated by reference in its entirety), as shown in FIG. 2. Therefore, to map the recognition sites of each antibody, polypeptides corresponding to different regions of human CstF-64 were expressed as fusions to glutathione S-transferase in bacteria and immunoblotted with either the 3A7 or 6A9 antibody.

Figure 3C:
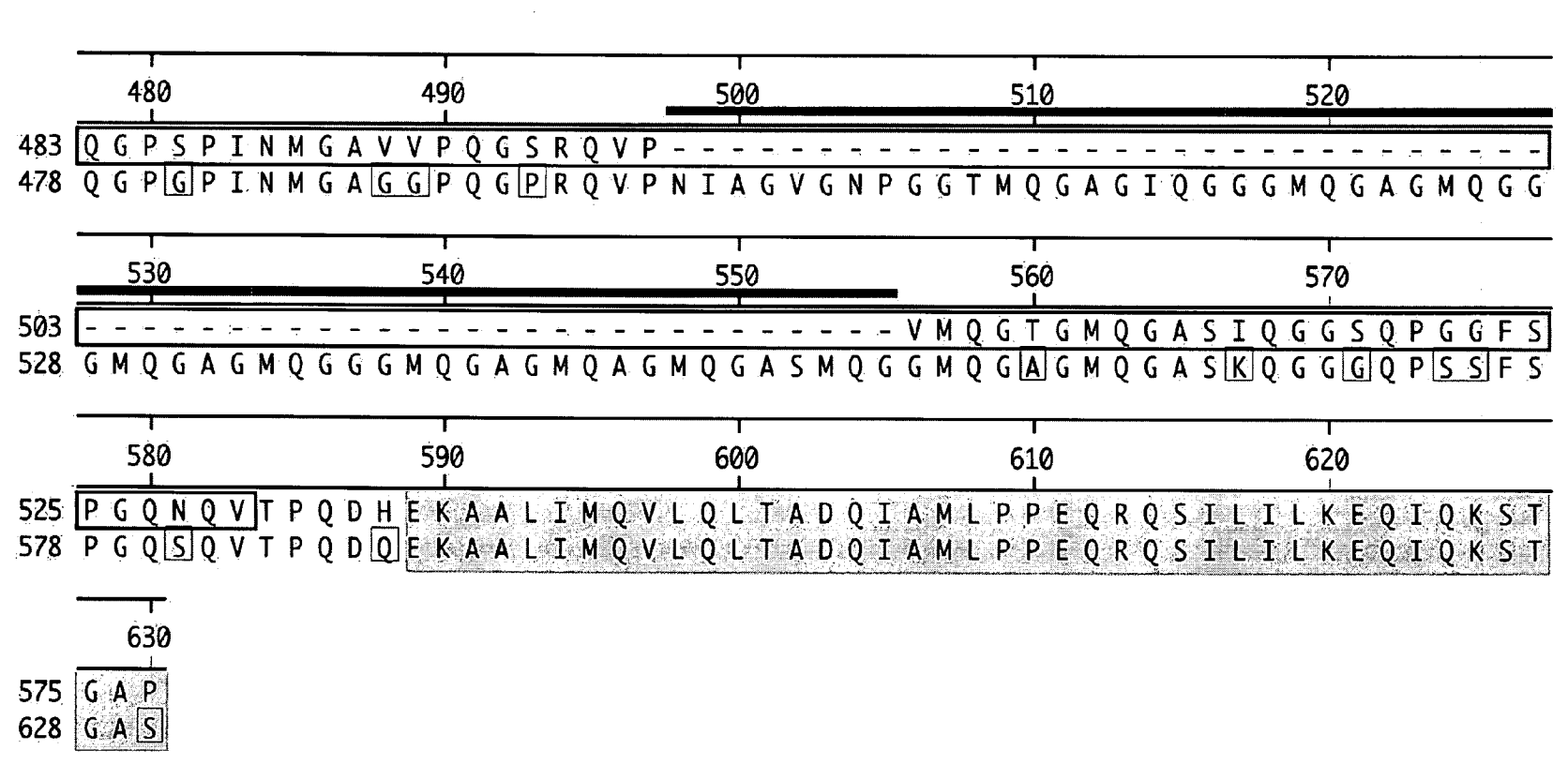

Using this approach, it was determined that the region where the 3A7 antibody interacted with CstF-64 lay between amino acids 426 and 531(441–583 as seen in FIGS. 3B–C). Since mτCstF-64 was recognized by the 6A9 antibody but not the 3A7 antibody (Wallace et al., "Two Distinct Forms of the 64,000 Mr Protein of the Cleavage Stimulation Factor are Expressed in Mouse Male Germ Cells," *Proc. Natl. Acad. Sci. USA* 96:6763–6768 (1999)), a mouse pachytene spermatocyte cDNA library was screened with the BamHI fragment of the human CstF-64 that includes the 6A9 epitope to isolate its cDNA.

Example 9

Isolation and Characterization of a cDNA for τCstF-64 From Mouse Pachytene Spermatocytes Two million plaques of an adult mouse pachytene spermatocyte library were screened using a 290-bp BamHI cDNA fragment of human CstF-64 encoding amino acids 316–412. Twenty-four positive clones were identified and rescued into pBluescript SK– (Stratagene, La Jolla, Calif.). Each of these plasmids represented nearly identical transcripts that differed in length at the 5' ends. None of the cDNAs represented the mouse somatic CstF-64. The plasmid containing the longest insert was designated mτCstF-64 (GenBank Accession Number AF322194, which is hereby incorporated by reference in its entirety) and was chosen for further characterization.

Sequence analysis of mτCstF-64 revealed a cDNA of 3595 bp and 16 bp of 3' poly (A). A single open reading frame (ORF) of 1890 bp was deduced that encoded a 630-amino acid protein with an estimated molecular mass of 65,898.8 Da and an isoelectric point of 7.10. The putative translation initiation codon ATG at nucleotide 77 is a good translational consensus. The mτCstF-64 cDNA had 76 bp of 5α-UTR and 1640 bp of 3'-UTR. There is a canonical polyadenylation sequence AATAAA at nucleotides 3576–3581.

Example 10

Characterization of the mτCstF-64 Protein

The protein encoded by the mτCstF-64 cDNA is similar to other known forms of CstF-64, and is 69.8 and 71.6% identical respectively, to the mouse and human somatic forms of CstF-64. The protein encoded by mτCstF-64 has two peptide inserts (amino acids 213–231 and 498–555) relative to the human, mouse and Xenopus proteins; these inserts are shared by the brain the protein encoded by KIAA0689, a cDNA of unknown function uncovered in a survey of long ORFs expressed in brain. These inserts probably account for the larger apparent molecular size of the variant CstF-64 protein seen on SDS-PAGE gels. The downstream insert (498–555) contains 12 imperfect repeats of the 5-amino acid motif MQG(A/G)G; two such repeats are seen in human CstF-64. Although it is unlikely that these repeats form a stabilized structure as the MAER(A/G) repeats in the human CstF-64 protein, it is possible they perform a similar, but undefined, function.

FIGS. 3A–C show an alignment of the mτCstF-64 protein with human (somatic) CstF-64. The mτCstF-64 protein shares features of known CstF-64 proteins as follows: an N-terminal RNA-binding domain (RBD) of the RNA recognition motif type (amino acids 17–92); proline- and glycine-rich regions (amino acids 198–425 and 464–579), a highly conserved C terminus (amino acids 589–630) and eight imperfect repeats of the amino acids MEAR(A/G) (amino acids 425–464) (Richardson et al., *Biochemistry* 38:12869–12875 (1999), which is hereby incorporated by reference in its entirety) that are repeated 12 times in human ((Takagaki et al., *Proc. Natl. Acad. Sci. U.S.A.* 89:1403–1407 (1992), which is hereby incorporated by reference in its entirety), mouse Dass et al., "The Gene for a Variant Form of the Polyadenylation Protein CstF-64 is on Chromosome 19 and is Expressed in Pachytene Spermatocytes in Mice," *J. Biol. Chem.* 276:8044–8050 (2001), which is hereby incorporated by reference in its entirety), and chicken CstF-64 (Takagaki et al., "Levels of Polyadenylation Factor CstF-64 Control IgM Heavy Chain mRNA Accumulation and Other Events Associated With B Cell Differentiation," *Mol. Cell* 2:761–771 (1998), which are hereby incorporated by reference in their entirety). The RBD of mτCstF-64 is identical to that of CstF-64 from human, mouse, and *Xenopus*, except for a serine replacing the proline at position 41 of the protein. FIG. 3D shows sequence identities (in percent) of known CstF-64 homologs. Shown are sequences from human (hCstF-64), mouse (mCstF-64), mouse τCstF-64 (mτCstF-64), human brain (KIAA0689), *Xenopus laevis* (xCstF-64), *Drosophila melanogaster* (dmCstF-64), *Caenorhabditis elegans* (ceCstF-64), and *Saccharomyces cerevisite* (yRNAl 5). Pairwise identities were determined from the alignments by CLUSTAL V method. FIG. 3E is a tree diagram showing the relative similarities of the human, mouse, bovine, *Xenopus*, *Caenorhabditis, Drosophila*, and yeast homologs of CstF-64.

Example 11

Antibody Reactivity of the mτCstF-64 Protein cDNA clones for CstF-64, mCstF-64, and mτCstF-64 were transcribed and translated in vitro using the rabbit reticulocyte lysate system, and proteins were tested for reactivity with the 3A7 and 6A9 monoclonal antibodies. As expected, CstF-64 from human reacted with both the 3A7 and 6A9 antibodies. CstF-64 from mouse reacted with 3A7, but not 6A9. This is in agreement with earlier assessments that the somatic form of CstF-64 from mouse is recognized by the 3A7 but not the 6A9 monoclonal antibody (Wallace et al., *Proc. Natl. Acad. Sci. U.S.A.* 96:6763–6768 (1999)). In contrast, the protein encoded by mτCstF-64 reacted with the 6A9 antibody, but not 3A7. Furthermore, the protein recognized by 6A9 had a larger apparent molecular weight than either the mouse or human somatic CstF-64 proteins. This suggests that mτCstF-64 has the same antibody reactivity as the variant form of CstF-64 found in mouse tests (Wallace et al., *Proc. Natl. Acad. Sci. U.S.A.* 96:6763–6768 (1999), which is hereby incorporated by reference in its entirety). The slowest migrating band of about 70 kDa in the human CstF-64 sample may be due to posttranslational modification, possibly phosphorylation (Takagaki et al., *Proc. Natl. Acad. Sci. U.S.A.* 89:1403–1407 (1992), which is hereby incorporated by reference in its entirety). The small amount of immunoreactivity in control samples that were incubated with vector DNA is probably due to endogenous CstF-64 protein in the rabbit lysates.

Example 12

Peptide Maps of the mτCstF-64 Protein Are Identical to the Pattern of the Variant CstF-64 from Testis To determine whether the protein encoded by mτCstF-64 is the same as that present in mouse testis, partial protease digestion patterns of the two proteins were compared. Radio-labeled mτCstF-64 protein was produced in vitro in rabbit reticulocyte lysate translation extracts in the presence of [$^{35}$S]methionine. Radio-labeled τCstF-64 was isolated in vivo by short term culture of mouse seminiferous tubules in medium containing [$^{35}$S]methionine followed by immunoprecipitation of the variant CstF-64 with the 6A9 antibody. Both proteins were treated identically with either 0.1 or 1.0 μg of *Staphylococcus aureus* V8 protease and analyzed by 15% SDS-PAGE and fluorography.

By comparing the partial protease digestion profiles of the protein synthesized in vitro with the protein synthesized in vivo, the two profiles appeared to share many common peptides. This suggests strongly that the two proteins share the same primary structure. In contrast, the protein encoded by the cDNA for the mouse somatic form of CstF-64, mCstF-64, has a distinctly different partial protease digestion profile, indicating that it has a different primary structure.

Example 13

Cstf2t is on Chromosome 19 in Mouse

The mouse chromosomal location for the mτCstF-64 gene (Cstf2t) was determined by interspecific backcross analysis using progeny derived from matings of ((C57BL/6J×*M. spretus*)F$_1$×C57BL/6J) mice. This interspecific backcross mapping panel has been typed for over 2900 loci that are well distributed among all the autosomes as well as the X chromosome (Copeland et al., *Trends Genet.* 7:113–118 (1991), which is hereby incorporated by reference in its entirety). C57BL/6J and *M. spretus* DNAs were digested with several enzymes and analyzed by Southern blot hybridization for informative restriction fragment length polymorphisms (RFLPs) using a mouse cDNA probe from mτCstF-64. A 1.8-kb TaqI *M. spretus* RFLP was used to follow the segregation of Cstf2t in backcross mice. The mapping results indicated that Cstf2t is located in the central region of mouse chromosome 19 linked to Gnaq and Fas. Although 120 mice were analyzed for every marker and are shown in the segregation analysis in FIG. 5, up to 167 mice were typed for some pairs of markers. Each locus was analyzed in pairwise combinations for recombination frequencies using the additional data. The ratios of the total number of mice exhibiting recombinant chromosomes to the total number of mice analyzed for each pair of loci and the most likely gene order are as follows: centromere-Gnaq-24/167-Cstf2t-1/122-Fas. The recombination frequencies (expressed as genetic distances in centimorgans±S.E.) are as follows: centromere-Gnaq-14.4±2.7-Cstf2t-0.8±0.8-Fas.

Example 14

RNA Binding of the mτCstF-64 Protein RBD

The RBDs of all vertebrate CstF-64s are identical except for mτCstF-64, which contains a single amino acid difference (amino acid 41), which raised the question of whether the mτCstF-64 RBD was functional in binding RNA in a UV cross-linking assay. The RNA-binding domains of human CstF-64 (amino acids 1–247), mouse CstF-64 (amino acids 1–247), and mτCstF-64 (amino acids 1–174) were incubated with $^{32}$P-labeled RNA in vitro and subjected to cross-linking with UV light (MacDonald et al., *Mol Cell. Biol.* 14:6647–6654 (1994); Takagaki et al., *Proc. Natl. Acad. Sci. U.S.A.* 89:1403–1407 (1992); Wilusz et al., *Cell* 52:221–228 (1988), which are hereby incorporated by reference in their entirety). Under the conditions used, each RBD-containing polypeptide bound covalently to RNA only in the presence of UV light. Minor differences in the intensity of the RNA cross-linked protein bands were not reproducible. In contrast, a non-RNA binding protein (IgG) did not bind to RNA irrespective of UV radiation. This suggests that all three RNA-binding domains are functional to bind a complex RNA substrate, although it does not address the question of RNA-binding specificity.

Example 15

Discussion of cDNA for mτCstF-64

Two forms of CstF-64 have been described that are expressed in distinctive patterns in mouse male germ cells. One form was clearly the somatic CstF-64 that is found in nearly every cell and tissue. The other had a more limited range and is designated mτCstF-64. It was hypothesized that, since the gene for the somatic form of CstF-64 (Cstf2) was located on the X chromosome and most X-linked genes are inactivated in male meiosis, mτCstF-64 was expressed from an autosomal paralog of CstF-64. The characterization cDNA for mτCstF-64 cloned from adult mouse pachytene spermatocytes and designated mτCstF-64 has been characterized as follows: (i) is found in a pachytene spermatocyte cDNA library, (ii) encodes a protein with an apparent mobility on SDS-PAGE of about $M_r$ 70,000, (iii) protein derived from this cDNA is recognized by the 6A9 but not the 3A7 monoclonal antibody, (iv) is encoded by the gene Cstf2t that is on an autosome, chromosome 19, (v) encodes a protein that has a partial peptide map that is identical to that of mτCstF-64 from testis, and (vi) is most similar to KIAA0689 (Ishikawa et al., "Prediction of the Coding Sequences of Unidentified Human Genes. X. The Complete Sequences of 100 New cDNA Clones from Brain Which Can Code for Large Proteins in vitro," *DNA Res.* 5(3):169–176 (1998), which is hereby incorporated by reference in its entirety), a cDNA from brain where mτCstF-64 is also found. It was also shown that the RBD of mτCstF-64 functions in RNA binding despite having a Pro→Ser substitution at amino acid 41 of the RBD.

Figure 5:
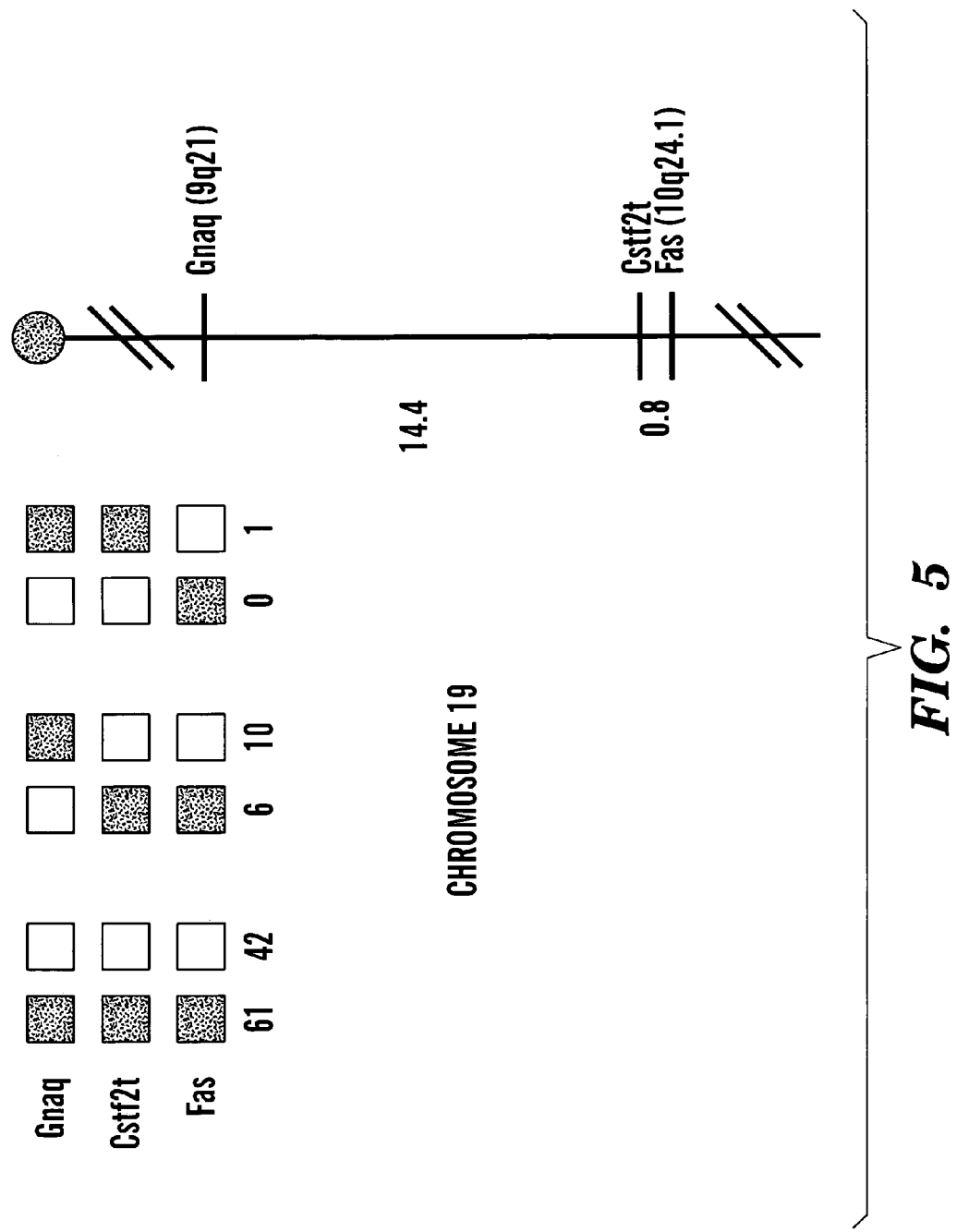
FIG. 5 is a diagram mapping the mτCstF-64 gene, Cstf2t, to mouse chromosome 19.

The mτCstF-64 protein is clearly the product of a different gene than is the mouse CstF-64 protein. The cDNAs are only 69.8% identical, leading to a number of amino acid substitutions throughout the protein, rather than inclusion or exclusion of individual exons. Furthermore, mouse backcross analysis determined that Cstf2t is on chromosome 19 (as shown in FIG. 5) and not the X chromosome as is Cstf2 (Wallace et al., "Two Distinct Forms of the 64,000 Mr Protein of the Cleavage Stimulation Factor are Expressed in Mouse Male Germ Cells," *Proc. Nati. Acad. Sci. USA* 96:6763–6768 (1999), which is hereby incorporated by reference in its entirety). A human cDNA clone, KIAA0689 (Ishikawa et al., "Prediction of the Coding Sequences of Unidentified Human Genes. X. The Complete Sequences of 100 New cDNA Clones from Brain Which Can Code for Large Proteins in vitro," *DNA Res.* 5(3):169–176 (1998), which is hereby incorporated by reference in its entirety), is quite similar to mτCstF-64 and is probably the human ortholog of this gene. These similarities between mτCstF-64 and the human and mouse somatic CstF-64s suggest that mτCstF-64 is the result of a duplication or retroviral insertion of the CstF-64I gene that occurred prior to the divergence of primates and mice (FIG. 3E).

As has been noted elsewhere, the C termini (amino acids 589–630) of all known CstF-64 homologs are remarkably conserved (Takagaki et al., "A Polyadenylation Factor Subunit is the Human Homologue of the *Drosophila* Suppressor of Forked Protein," *Nature* 372:471–474 (1994); Takagaki et al., "The Human 64-kDa Polyadenylation Factor Contains a Ribonucleoprotein-type RNA Binding Domain and Unusual Auxiliary Motifs," *Proc. Natl. Acad. Sci. USA* 89(4):1403–1407 (1992); Dass et al., "Overexpression of the CstF-64 and CPSF-160 Polyadenylation Protein Messenger RNAs in Mouse Male Germ Cells," *Biol. Reprod.* 64(6): 1722–1729 (2001); Ishikawa et al., "Prediction of the Coding Sequences of Unidentified Human Genes. X. The Complete Sequences of 100 New cDNA Clones from Brain Which Can Code for Large Proteins in vitro," *DNA Res.* 5(3):169–176 (1998), Hatton et al., "The *Drosophila* Homologue of the 64 kDa Subunit of Cleavage Stimulation Factor Interacts with the 77 kDa Subunit Encoded by the Suppressor of Forked Gene," *Nucleic Acids Res.* 28(2):520–526 (2000), and Barbaux et al., "The *Xenopus Laevis* Homologue of the 64-kDa Subunit of Cleavage Stimulation Factor," *Comp. Biochem. Physiol. B. Comp. Biochem. Mol. Biol.* 114(3):313–315 (1996); which are hereby incorporated by reference in their entirety), suggesting an essential function for that region. Also conserved is the RNA recognition motif type RNA-binding domain at the N terminus, which is identical in all vertebrate CstF-64s examined: human (Takagaki et al., "The Human 64-kDa Polyadenylation Factor Contains a Ribonucleoprotein-type RNA Binding Domain and Unusual Auxiliary Motifs," *Proc. Natl. Acad. Sci. USA* 89(4):1403–1407 (1992), which is hereby incorporated by reference in its entirety), mouse (Dass et al., "Overexpression of the CstF-64 and CPSF-160 Polyadenylation Protein Messenger RNAs in Mouse Male Germ Cells," *Biol. Reprod.* 64(6):1722–1729 (2001), which is hereby incorporated by reference in its entirety), Xenopus (Barbaux et al., "The *Xenopus Laevis* Homologue of the 64-kDa Subunit of Cleavage Stimulation Factor," *Comp. Biochem. Physiol. B. Comp. Biochem. Mol. Biol.* 114(3):313–315 (1996), which is hereby incorporated by reference in its entirety), and chicken (Takagaki et al., "The Polyadenylation Factor CstF-64 Regulates Alternative Processing of IgM Heavy Chain Pre-mRNA During B Cell Differentiation," *Cell* 87(5):941–952 (1996), which is hereby incorporated by reference in its entirety), except mτCstF-64, which has a single proline→serine change at amino acid 41. RBDs of the RNA recognition motif type have a well defined βαββαβ motif (Burd et al., "Conserved Structures and Diversity of Functions of RNA-Binding Proteins," *Science* 265(5172):615–621 (1994); Nagai et al., "Crystal Structure of the RNA-Binding Domain of the U1 Small Nuclear Ribonucleoprotein A," *Nature* 348(6301):515–520 (1990); Nagai et al., "Crystal Structure of the RNA-Binding Domain of the U1 Small Nuclear Ribonucleoprotein A," *Nature* 348(6301):515–520 (1990), which are hereby incorporated by reference in their entirety), and serine 41 is part of the second loop following the first α-helix in the RBD that might alter RNA substrate specificity (Nagata et al., "Structure and Interactions with RNA of the N-Terminal UUAG-Specific RNA-Binding Domain of hnRNP D0," *J. Mol. Biol.* 287(2):221–237 (1999), which is hereby incorporated by reference in its entirety). Therefore, mτCstF-64 might have a different RNA binding specificity than CstF-64, which would contribute to the differences seen in germ cell polyadenylation.

Many of the animo acid subtitutions in mτCstF-64 relative to Cstf-64 are in regions that have as yet unknown functions, including the Gly/Pro-rich regions (FIGS. 3A–C, amino acids 198–425 and 464–579 (Takagaki et al., "The Human 64-kDa Polyadenylation Factor Contains a Ribonucleoprotein-type RNA Binding Domain and Unusual Auxiliary Motifs," *Proc. Nati. Acad. Sci. USA* 89(4):1403–1407 (1992), which is hereby incorporated by reference in its entirety). Interestingly, a number of substitutions and a 19-amino acid insertion occur in the region thought to interact with CstF-77 (FIGS. 3A–B, amino acids 180–260, summarized in FIG. 6), which bridges CstF and CPSF, and symplekin, a protein whose function in the nucleus is not known (Takagaki et al., "Complex Protein Interactions Within the Human Polyadenylation Machinery Identify a Novel Component," *Mol. Cell Biol.* 20(5): 1515–1525 (2000), which is hereby incorporated by reference in its entirety). This suggests the possibility that mτCstF-64 interacts differently than CstF-64 with other proteins of the polyadenylation complex, and the interaction might affect mτCstF-64 function in germ cell polyadenylation.

The MEAR(A/G) repeat region of mτCstF-64 is significantly different than the 12 repeats in CstF-64 (Takagaki et al., "The Human 64-kDa Polyadenylation Factor Contains a Ribonucleoprotein-type RNA Binding Domain and Unusual Auxiliary Motifs," *Proc. Natl. Acad. Sci. USA* 89(4):1403–1407 (1992), Richardson et al., "MEARA Sequence Repeat of Human CstF-64 Polyadenylation Factor is Helical in Solution. A Spectroscopic and Calorimetric Study," *Biochemistry* 38(39):12869–12875 (1999), which are hereby incorporated by reference in their entirety). The region in mτCstF-64 contains only eight recognizable repeats (425–464), one of which is incomplete (441–444), some of which have proline substitutions (430, 438), and none of which precisely match the consensus. In CstF-64, the MEAR(A/G) repeats likely form a stable, monomeric α-helix that might serve as a rigid structural element in polyadenylation (Richardson et al., "MEARA Sequence Repeat of Human CstF-64 Polyadenylation Factor is Helical in Solution. A Spectroscopic and Calorimetric Study," *Biochemistry* 38(39):12869–12875 (1999), which is hereby incorporated by reference in its entirety). Perhaps the degenerate MEAR(A/G) region in mτCstF-64 forms a shorter structural variant or is dispensable, as it is in *Xenopus*, which lacks MEAR(A/G) (Barbaux et al., "The *Xenopus Laevis* Homologue of the 64-kDa Subunit of Cleavage Stimulation Factor," *Comp. Biochem. Physiol. B. Comp. Biochem. Mol. Biol.* 114(3):313–315 (1996), which is hereby incorporated by reference in its entirety). However, the second insert in mτCstF-64 (498–555) includes 12 repeats of the amino acids MQG(A/G)G that might substitute for the MEAR(A/G) function.

Figure 7:
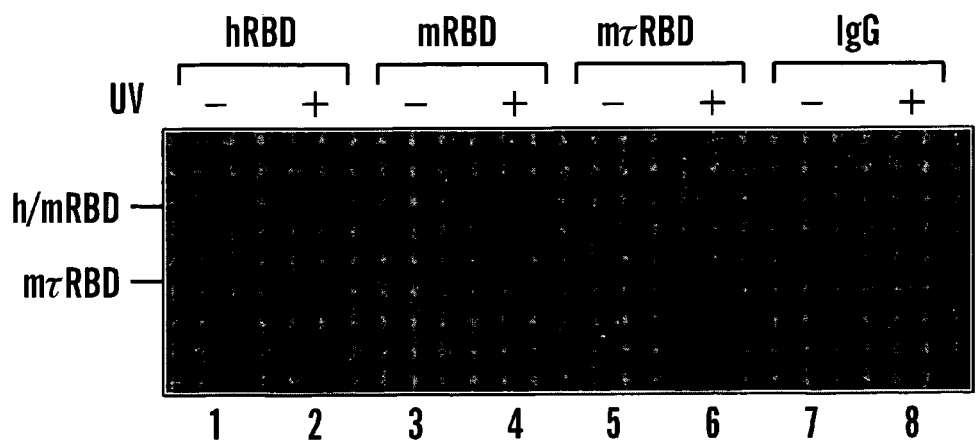
FIG. 7 shows RNA binding of RBDs from different CstF-64 proteins.

How might mτCstF-64 be involved in promoting polyadenylation of non-AAUAAA-containing mRNAs in male germ cells? One possibility is that the Pro→Ser substitution at amino acid 41 alters the RNA binding affinity of the variant CstF-64 (Beyer et al., "RNA Ligands Selected by Cleavage Stimulation Factor Contain Distinct Sequence Motifs that Function as Downstream Elements in 3'-End Processing of Pre-mRNA," *J. Biol. Chem.* 272(42):26769–26779 (1997); Takagaki et al., "RNA Recognition by the Human Polyadenylation Factor CstF," *Mol. Cell Biol.* 17(7):3907–3914 (1997), which are hereby incorporated by reference in their entirety), allowing binding to a different downstream sequence element (MacDonald et al., "The 64-Kilodalton Subunit of the CstF Polyadenylation Factor Binds to Pre-mRNAs Downstream of the Cleavage Site and Influences Cleavage Site Location," *Mol. Cell. Biol.* 14(10):6647–6654 (1994), which is hereby incorporated by reference in its entirety). An altered affinity of CstF for a downstream sequence element could then influence the binding of CPSF to an upstream element, which might or might not match the AAUAAA consensus. RNA binding experiments, shown in FIG. 7, suggest that mammalian CstF-64 RBDs have similar affinities for nonspecific RNAs. However, the RNA binding specificity of CstF-64 is quite different in isolation than in complex with CstF-77, CstF-50, and CPSF (MacDonald et al., "The 64-Kilodalton Subunit of the CstF Polyadenylation Factor Binds to Pre-mRNAs Downstream of the Cleavage Site and Influences Cleavage Site Location," *Mol. Cell. Biol.* 14(10):6647–6654 (1994); Wilusz et al., "A Multicomponent Complex is Required for the AAUAAA-Dependent Cross-Linking of a 64-kilodalton Protein to Polyadenylation Substrates," *Mol. Cell. Biol.* 10:1244–1248 (1990), which are hereby incorporated by reference in their entirety). Therefore, other regions of mτCstF-64 and other interacting proteins might have a strong influence on RNA substrate specificity. In light of this, mτCstF-64 contains a number of amino acid differences in the site of protein-protein interaction with CstF-77 and symplekin. Changes in this region (FIG. 3A, amino acids 108–229) could disrupt binding of CstF-64 to CstF-77 or even to symplekin, thus dramatically altering CstF interaction with the pre-mRNA and with CPSF.

Example 16

Complementary DNA Cloning of the Human Variant CstF-64 (hτCstF-64)

$2 \times 10^6$ pfu of a human testis cDNA library in Lambda ZAP Express EcoRI/XhoI vector (Stratagene, La Jolla, Calif.) was screened using an 850 bp EcoRI fragment from the 5' end of mouse τCstF-64 cDNA (nucleotides 43–885; Dass et al., "The Gene for a Variant Form of the Polyadenylation Protein CstF-64 is on Chromosome 19 and is Expressed in Pachytene Spermatocytes in Mice," *J. Biol. Chem.* 276: 8044–8050 (2001), which is hereby incorporated by reference in its entirety). Plaque lifts and library screening were exactly as described in Dass et al., "The Gene for a Variant Form of the Polyadenylation Protein CstF-64 is on Chromosome 19 and is Expressed in Pachytene Spermatocytes in Mice," *J. Biol. Chem.* 276:8044–8050 (2001), which is hereby incorporated by reference in its entirety. Thirty-eight positive plaques were identified and purified by two additional rounds of screening. Plasmids were rescued into pBK-CMV according to the manufacturer's directions (Stratagene, La Jolla, Calif.), digested with EcoRI and XhoI, separated by agarose gel electrophoresis and subjected to Southern blot analysis with an $\alpha[^{32}P]dCTP$-labeled 140 bp KpnI-NheI cDNA fragment from mouse τCstF-64 (nucleotides 1598–1727 (Dass et al., "The Gene for a Variant Form of the Polyadenylation Protein CstF-64 is on Chromosome 19 and is Expressed in Pachytene Spermatocytes in Mice," *J. Biol. Chem.* 276:8044–8050 (2001), which is hereby incorporated by reference in its entirety). Three of the 38 clones were positive with this probe, and were designated human τCstF-64 (hτCstF-64) based on sequence.

Example 17

Figure 8A:
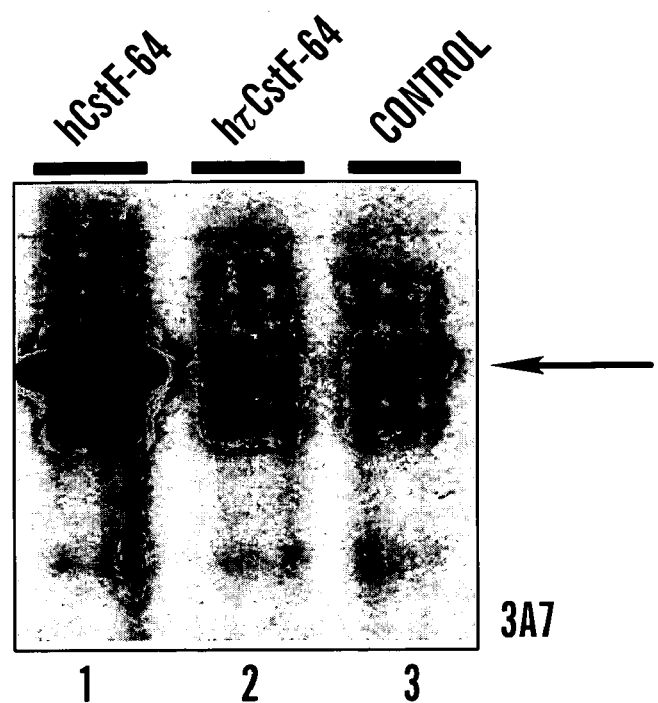
FIGS. 8A–B are SDS-PAGE results showing antibody recognition of the protein encoded by hτCstF-64. Plasmids containing cDNA clones of hCstF-64 (lanes 1), hτCstF-64 (lanes 2), or no plasmid (control, lanes 3) were added to coupled transcription and translation extracts to obtain the corresponding proteins. Proteins were separated by 10% SDS-PAGE and immunoblots were incubated with either monoclonal antibody 3A7, shown in FIG. 8A, or 6A9, shown in FIG. 8B. Arrows indicate CstF-64 protein products at the right.

In Vitro Transcription and Translation cDNAs encoding hCstF-64 (Takagaki et al., "The Human 64-kDa Polyadenylation Factor Contains a Ribonucleoprotein-Type RNA Binding Domain and Unusual Auxiliary Motifs," *Proc. Natl. Acad. Sci. USA* 89:1403–1407 (1992), which is hereby incorporated by reference in its entirety) and hτCstF-64 were transcribed and translated using T7 and T3 TNT Coupled reticulocyte lysate systems (Promega, Madison, Wis.), respectively. Lysate proteins were separated on 10% SDS-PAGE gels and immunoblotted with either the 3A7, shown in FIG. 8A, or 6A9 monoclonal antibody, shown in FIG. 8B (Takagaki et al., "A Multisubunit Factor CstF is Required for Polyadenylation of Mammalian pre-mRNAs," *Genes Dev.* 4:2112–2120 (1990)) according to Wallace et al., "Two Distinct Forms of the 64,000 $M_r$ Protein of the Cleavage Stimulation Factor are Expressed in Mouse Male Germ Cells," *Proc. Natl. Acad. Sci. USA* 96:6763–6768 (1999), which is hereby incorporated by reference in its entirety. The control lysate contained no exogenous plasmid DNA.

Example 18

PCR-Based Chromosomal Assignment

PCR using gene-specific primers was used to analyze the presence of the hτCstF-64 gene. The primers used were:

```
(1) 5'-GCTCTGCCCAGGACCTAATGTTC-3'      (698-720, sense);        (SEQ ID NO: 5)

(2) 5'-TTGTCCCCGCTCTAAAGGCACTGGG-3'    (950-927, antisense);    (SEQ ID NO: 6)

(3) 5'-CCACGTGGAGGGACTITTGCTTTCA-3'    (1047-1070, sense);      (SEQ ID NO: 7)

(4) 5'-TGCCCCTTGCTTCCATCCCTCTG-3'      (1395-1373, antisense);  (SEQ ID NO: 8)

(5) 5'-CACCICATCAGGGYCCICCIATGCAYCA-3' (sense)                  (SEQ ID NO: 9)

(6) 5'-TGRTCYGCAGTIAGYTGIAGIACCTGCAT-3' (antisense),            (SEQ ID NO: 10)

where Y = C or T, R = A or G, I = inosine.
```

The expected size of PCR products was 252 bp for primer pair (1 and 2) and 347 bp for primer pair (3 and 4). PCR was performed using a Light Cycler thermal cycler (Idaho Technology, Idaho Falls, Id.) and contained 50 ng of genomic DNA and 4 mM magnesium under the following conditions: denature 94° C. (2 min.); thirty cycles of [94° C. (1 min.), 65° C. (primer pair 1 and 2, 30 sec.) or 70° C. (primer pair 3 and 4, 30 sec.), 72° C. (30 sec.)]; 72° C. (2 min.). Templates were mouse-human hybrid cell DNA monochromosomal for human chromosome 9, mouse-human hybrid cell DNA monochromosomal for human chromosome 10, total human genomic DNA, and total mouse genomic DNA.

PCR reactions were separated on a 1% agarose/TBE gel and visualized by ethidium bromide staining in the presence of UV light.

Example 19

Radiation Hybrid Analysis

Human τCstF-64-specific primers (1) and (4) were used to screen a GeneBridge 4 whole-genome radiation hybrid panel (Research Genetics, Carlsbad, Calif.) consisting of 93 genomic DNAs from human-on-hamster somatic cell lines (Gyapay et al., "A Radiation Hybrid Map of the Human Genome," *Hum. Mol. Genet.* 5:339–346 (1996), which is hereby incorporated by reference in its entirety). Twenty nanograms of genomic DNA were used in each reaction. Results were submitted to the Whitehead Institute/MIT Center for Genome Research's sequence-tagged sites mapping Web server (http://www.genome.wi.mit.edu/cgi-bin/contig/rhmapper) with a LOD score of 15.

Example 20

Isolation of a cDNA for the Variant CstF-64 from Human Testis

A human testis cDNA library made from pooled RNA samples of four Caucasian male subjects (Stratagene, La Jolla, Calif.) was screened to obtain a full length cDNA for the human variant CstF-64 (GenBank accession number AY130299) using a probe from the RNA-binding domain of mouse τCstF-64 (Dass et al., "The Gene for a Variant Form of the Polyadenylation Protein CstF-64 is on Chromosome 19 and is Expressed in Pachytene Spermatocytes in Mice," *J. Biol. Chem.* 276:8044–8050 (2001), which is hereby incorporated by reference in its entirety). Two million recombinant phages were screened, of which thirty-eight hybridized to the probe. Phages were rescued into pBK-CMV plasmids by the manufacturer's protocol (Stratagene, La Jolla, Calif.). Most of these were shown to be the somatic CstF-64 by Southern blot analysis. However, Southern blot analysis revealed that three of the clones contained the second insert region found in mτCstF-64 (nucleotides 1598–1727; Dass et al., "The Gene for a Variant Form of the Polyadenylation Protein CstF-64 is on Chromosome 19 and is Expressed in Pachytene Spermatocytes in Mice," *J. Biol. Chem.* 276:8044–8050 (2001), which is hereby incorporated by reference in its entirety). The plasmid containing the longest cDNA insert was designated hτCstF-64 and chosen for further analysis.

Sequence analysis revealed that hτCstF-64 had an insert of 2333 bp that included 17 bp of poly(A) tail at the 3' end. There was a single open reading frame (ORF) of 1850 bp encoding a 616 amino acid protein with an estimated molecular mass of 64,435.8 and an isoelectric point of 7.11. The putative translation initiation codon, AUG at nucleotide 39, appears to be in reasonable Kozak consensus (though lacking a G at position +4)(Kozak, M., "The Scanning Model for Translation: An Update," *J. Cell Biol.* 108: 29–241 (1965); Kozak, M., "Recognition of AUG and Alternative Initiator Codons is Augmented by G in Position +4 but is Not Generally Affected by the Nucleotides in Positions +5 and +6," *EMBO J.* 16:2482–2492 (1997), which are hereby incorporated by reference in their entirety). The full-length clone had a 38 bp 5' UTR (nucleotides 1–38) and a 434 bp 3' UTR (nucleotides 1890–2324). There is a putative polyadenylation signal (AAUAAA) at nucleotides 2310–2315.

The protein encoded by hτCstF-64 is closely related to the other CstF-64 homologs, including mouse (Dass et al., "The Gene for a Variant Form of the Polyadenylation Protein CstF-64 is on Chromosome 19 and is Expressed in Pachytene Spermatocytes in Mice," *J. Biol. Chem.* 276: 8044–8050 (2001), which is hereby incorporated by reference in its entirety); human (Takagaki et al., "The Human 64-kDa Polyadenylation Factor Contains a Ribonucleoprotein-Type RNA Binding Domain and Unusual Auxiliary Motifs," *Proc. Natl. Acad. Sci. USA* 89:1403–1407 (1992), which is hereby incorporated by reference in its entirety); *Drosophila melanogaster* (Hatton et al., "The *Drosophila* Homologue of the 64 kDa Subunit of Cleavage Stimulation Factor Interacts With the 77 kDa Subunit Encoded by the Suppressor of Forked Gene," *Nucl. Acids Res.* 28:520–526 (2000), which is hereby incorporated by reference in its entirety); *Xenopus Laevis* (Barbaux et al., "The *Xenopus Laevis* Homologue of the 64-kDa Subunit of Cleavage Stimulation Factor," *Comp. Biochem. Physiol. B Biochem. Mol. Biol.* 114B:313–315 (1996), which is hereby incorporated by reference in its entirety); *Saccharomyces cerevisiae* (Takagaki et al., "A Polyadenylation Factor Subunit is the Human Homologue of the *Drosophila* Suppressor of Forked Protein," *Nature* 372:471–474 (1994), which is hereby incorporated by reference in its entirety), *Caenorhabditis elegans* (Evans et al., "A Complex Containing CstF-64 and the SL2 snRNP Connects mRNA 3' End Formation and Trans-Splicing in *C. Elegans* Operons," *Genes Dev.* 15:2562–2571 (2001), which is hereby incorporated by reference in its entirety) and is most similar to bovine (GenBank Accession number AY130298, which is hereby incorporated by reference in its entirety) and mouse τCstF-64s (Dass et al., "The Gene for a Variant Form of the Polyadenylation Protein CstF-64 is on Chromosome 19 and is Expressed in Pachytene Spermatocytes in Mice," *J. Biol. Chem.* 276:8044–8050 (2001), which is hereby incorporated by reference in its entirety) (89.8% and 87.4%, respectively, shown in FIG. 4B and FIG. 6). Interestingly, hτCstF-64 was nearly identical to a human cDNA, KIAA 0689 that was identified in a screen to find long open reading frames in human brain (Ishikawa et al., "Prediction of the Coding Sequences of Unidentified Human Genes. X. The Complete Sequences of 100 New cDNA Clones From Brain Which Can Code for Large Proteins in Vitro," *DNA Res.* 5:169–176 (1998), which is hereby incorporated by reference in its entirety). When its sequence was aligned with that of hτCstF-64, KIAA 0689 was truncated at the 5' end, but contained a much longer 3' UTR.

Figure 4B:
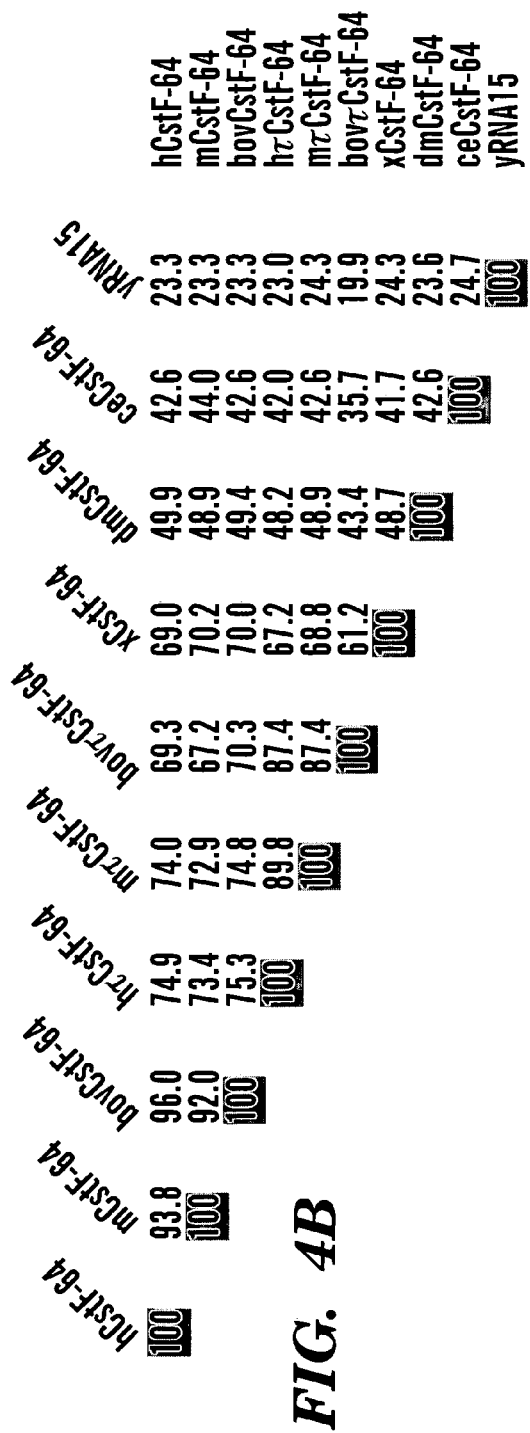
Figure 4C:
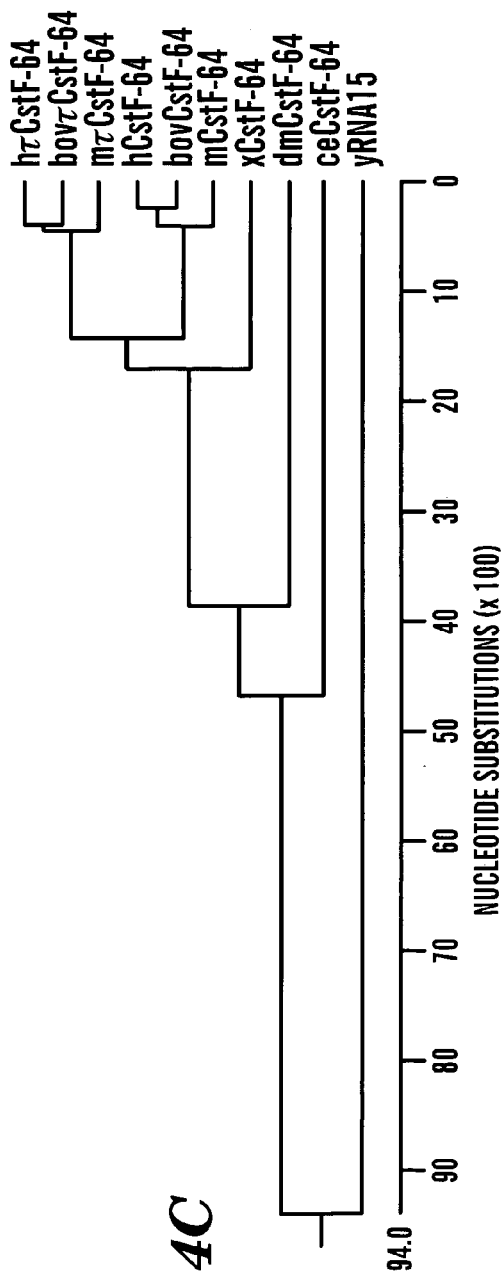
Figure 6:
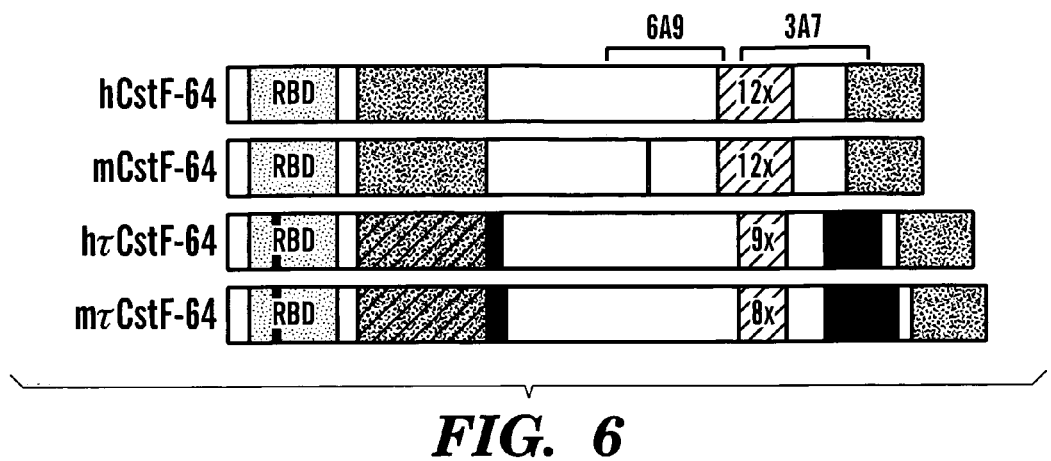
FIG. 6 is an alignment of domains of interest in human and mouse CstF-64 and variant CstF-64 proteins. Diagrams are of hCstF-64 (577 amino acids), mCstF-64 (580 amino acids), hτCstF-64 (616 amino acids), and mτCstF-64 (630 amino acids), with features as indicated. Shown are the RNA-binding domains (RBD, light gray), the region of interaction with CstF-77 (dark gray), MEARA repeats (hatched) and the conserved C-terminal domain (dark gray). The proline→serine change at amino acid 41 within the RBD is indicated as a dark gray bar, and regions of hτCstF-64 and mτCstF-64 corresponding to the CstF-77 interaction domain are gray and hatched to indicate their divergence from hCstF-64. Inserted domains relative to hCstF-64 are indicated as black.

The protein encoded by hτCstF-64 shares several features in common with the other mammalian CstF-64 homologs, as shown in FIGS. 4B and 4C, and summarized in FIG. 6. It has an N-terminal RNA-binding domain of the RRM type (amino acids 17–92) (Burd et al., "Conserved Structures and Diversity of Functions of RNA-Binding Proteins," *Science* 265:615–621 (1994), which is hereby incorporated by reference in its entirety) that is identical to that of mouse τCstF-64 including the proline→serine change at amino acid 41, and which differs from the somatic CstF-64 from human (Takagaki et al., "The Human 64-kDa Polyadenylation Factor Contains a Ribonucleoprotein-Type RNA Binding Domain and Unusual Auxiliary Motifs," *Proc. Natl. Acad. Sci. USA* 89:1403–1407 (1992), which is hereby incorporated by reference in its entirety), mouse (Dass et al., "The Gene for a Variant Form of the Polyadenylation Protein CstF-64 is on Chromosome 19 and is Expressed in Pachytene Spermatocytes in Mice," *J. Biol. Chem.* 276: 8044–8050 (2001), which is hereby incorporated by reference in its entirety), bovine (Dass et al., "The Gene CSTF2T, Encoding the Human Varian CstF-64 Polyadenylation Protein τCstF-64, Lacks Introns and May Be Associated with Male Sterility," *Genomics* 80(5):1–6 (2002), which is hereby incorporated by reference in its entirety), and *Xenopus* (Barbaux et al., "The *Xenopus Laevis* Homologue of the 64-kDa Subunit of Cleavage Stimulation Factor," *Comp. Biochem. Physiol. B Biochem. Mol. Biol.* 114B:313–315 (1996), which is hereby incorporated by reference in its entirety). Human τCstF-64 has two insert regions that are missing from the somatic homologs, but that are present in mouse τCstF-64, seen in FIG. 4A and summarized in FIG. 6. These inserts allow hτCstF-64 to encode a protein that is larger than the $M_r$ 64,000 somatic CstF-64 (Wallace et al., "Two Distinct Forms of the 64,000 $M_r$ Protein of the Cleavage Stimulation Factor are Expressed in Mouse Male Germ Cells," *Proc. Natl. Acad. Sci. USA* 96:6763–6768 (1999); Dass et al., "The Gene for a Variant Form of the Polyadenylation Protein CstF-64 is on Chromosome 19 and is Expressed in Pachytene Spermatocytes in Mice," *J. Biol. Chem.* 276:8044–8050 (2001), which are hereby incorporated by reference in their entirety). Human τCstF-64 has nine identifiable MEARA/G repeats (amino acids 418–462) (Richardson et al., "MEARA Sequence Repeat of Human CstF-64 Polyadenylation Factor is Helical in Solution. A Spectroscopic and Calorimetric Study," *Biochemistry* 38:12869–12875 (1999), which is hereby incorporated by reference in its entirety) compared to eight in mouse τCstF-64 (Dass et al., "The Gene for a Variant Form of the Polyadenylation Protein CstF-64 is on Chromosome 19 and is Expressed in Pachytene Spermatocytes in Mice," *J. Biol. Chem.* 276:8044–8050 (2001), which is hereby incorporated by reference in its entirety), and twelve in human, mouse and chicken somatic CstF-64 (Takagaki et al., "The Human 64-kDa Polyadenylation Factor Contains a Ribonucleoprotein-Type RNA Binding Domain and Unusual Auxiliary Motifs," *Proc. Natl. Acad. Sci. USA* 89:1403–1407 (1992); Dass et al., "Overexpression of the CstF-64 and CPSF-160 Polyadenylation Protein Messenger RNAs in Mouse Male Germ Cells," *Biol. Reprod.* 64:1722–1729 (2001); Takagaki et al., "Levels of Polyadenylation Factor CstF-64 Control IgM Heavy Chain mRNA Accumulation and Other Events Associated With B Cell Differentiation," *Mol. Cell* 2:761–771 (1998), which are hereby incorporated by reference in their entirety). Finally, hτCstF-64 shares the highly conserved C-terminal domain (amino acids 575–616) that is seen in the other known CstF-64 homologs (Hatton et al., "The *Drosophila* Homologue of the 64 kDa Subunit of Cleavage Stimulation Factor Interacts With the 77 kDa Subunit Encoded by the Suppressor of Forked Gene," *Nucl. Acids Res.* 28:520–526 (2000), which is hereby incorporated by reference in its entirety) and which might interact with the transcriptional coactivator PC4 (Calvo et al., "Evolutionarily Conserved Interaction Between CstF-64 and PC4 Links Transcription, Polyadenylation, and Termination," *Mol. Cell* 7:1013–1023 (2001), which is hereby incorporated by reference in its entirety).

Example 21

Antibody Reactivity of Protein Encoded by hτCstF-64 cDNA

Figure 8B:
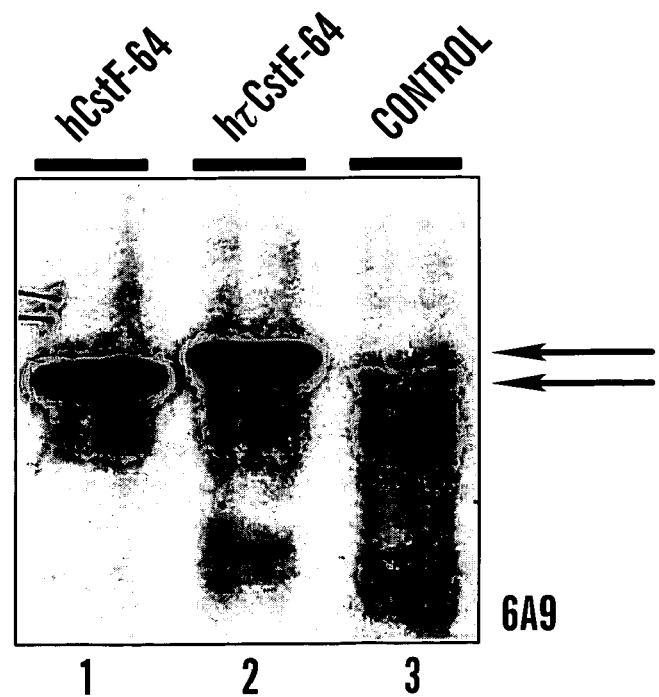

It was previously noted that the 3A7 antibody recognized mouse somatic CstF-64, while the 6A9 antibody recognized τCstF-64 (Wallace et al., "Two Distinct Forms of the 64,000 $M_r$ Protein of the Cleavage Stimulation Factor are Expressed in Mouse Male Germ Cells," *Proc. Natl. Acad. Sci. USA* 96:6763–6768 (1999); Dass et al., "The Gene for a Variant Form of the Polyadenylation Protein CstF-64 is on Chromosome 19 and is Expressed in Pachytene Spermatocytes in Mice," *J. Biol. Chem.* 276:8044–8050 (2001), which are hereby incorporated by reference in their entirety), and it was desirable to make the same determination for the human CstF-64 and τCstF-64 proteins. Complementary DNAs encoding either hCstF-64 or hτCstF-64 were added to rabbit reticulocyte lysates (Promega, Madison, Wis.) to obtain the corresponding protein by in vitro transcription and translation (Dass et al., "The Gene for a Variant Form of the Polyadenylation Protein CstF-64 is on Chromosome 19 and is Expressed in Pachytene Spermatocytes in Mice," *J. Biol. Chem.* 276:8044–8050 (2001), which is hereby incorporated by reference in its entirety). Lysates were separated by SDS-PAGE and immunoblotted with either the 3A7 or 6A9 monoclonal antibody, shown in FIGS. 8A–B. In agreement with earlier data, the protein encoded by the human CstF-64 cDNA was recognized by both the 3A7, shown in FIG. 8A, lane 1, and the 6A9 antibodies, shown in FIG. 8B, lane 1. However, the protein encoded by the human τCstF-64 cDNA was recognized by the 6A9 monoclonal, shown in FIG. 8B, lane 2, but not by 3A7, shown in FIG. 8A, lane 2. Human τCstF-64 also migrates more slowly than CstF-64, shown in FIG. 8B, compare lanes 1 and 2, consistent with its larger predicted size, shown in FIG. 4A and FIG. 6. The low level of reactivity seen in the control lane that is not programmed with any cDNA, shown in FIGS. 8A, B lanes 3, is likely due to endogenous CstF-64 protein from the rabbit reticulocyte lysate.

Example 22

CSTF2T, Gene for hτCstF-64 is on Human Chromosome 10

Figure 9:
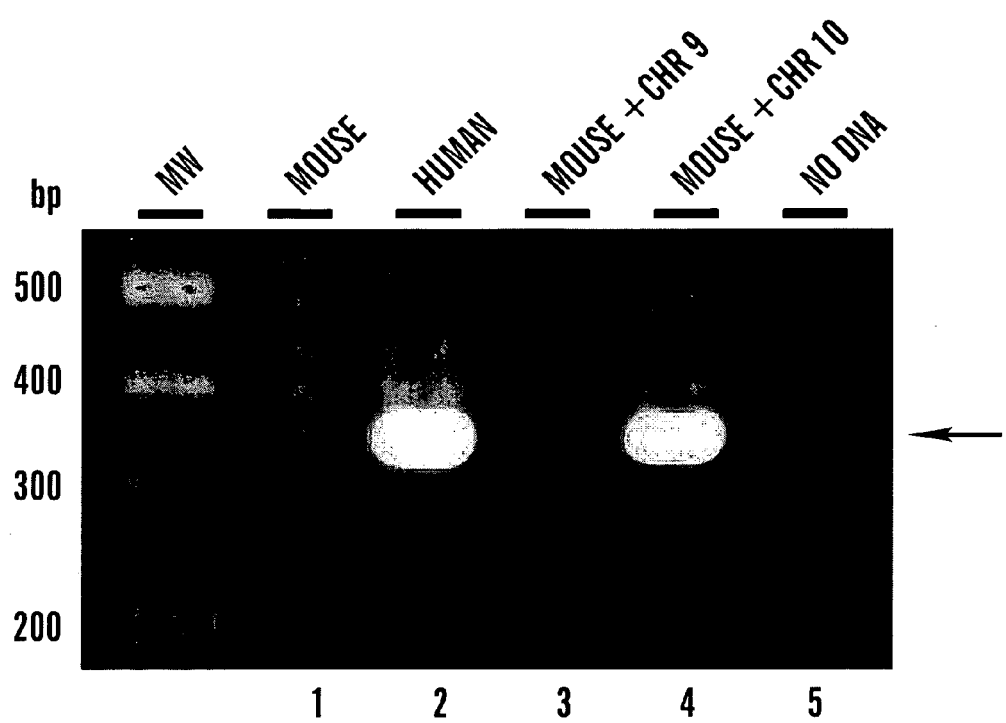
FIG. 9 is a PCR-based chromosomal assignment of CSTF2T to human chromosome 10. PCR using primer pairs (3 and 4) was performed on 50 ng of DNA from mouse (lane 1), human (lane 2), a mouse cell line monochromosomal for human chromosome 9 (lane 3), or human chromosome 10 (lane 4), or with no input DNA (lane 5). The arrow (right) indicates the 347-bp PCR reaction product expected for this primer pair. Identical results were seen with primer pair (1 and 2). Molecular weight markers are at the left.

Mouse Cstf2t mapped to a region of chromosome 19 with homology to both human chromosome 9 and 10. PCR was used to determine which chromosome was more likely to contain the human CSTF2T. Using DNA from a mouse hybrid cell line that was monochromosomal for human chromosome 9 or 10, PCR was performed with primer pair (3) and (4) under conditions specific for the amplification of human variant CstF-64 DNA. No PCR product was seen from wild-type mouse DNA, as shown in FIG. 9, lane 1, while a 342-bp fragment was seen with human DNA (lane 2), confirming that the PCR primer pairs and conditions were specific to human τCstF-64. Little or no PCR product was seen from DNA monochromosomal for chromosome 9 (lane 3), but product of the expected size was obtained from DNA monochromosomal for chromosome 10 (lane 4). Identical results were seen using PCR primer pair (1 and 2). This indicates that CSTF2T, the gene for hτCstF-64 was located on human chromosome 10. The CSTF2T locus thus obtained was syntenic to the locus for the mτCstF-64 gene, Cstf2t on mouse chromosome 19 and supports the hypothesis that CSTF2T is the human ortholog of Cstf2t.

Example 23

Radiation Hybrid Analysis Maps CSTF2T to 10q22–23

PCR using primers (1) and (4) was used to determine sequence-tagged sites for CSTF2T by radiation hybrid analysis in the GeneBridge 4 bank of human-on-hamster somatic cell hybrid genomic DNAs and submitted to the Whitehead Institute/MIT Center for Genome Research's sequence-tagged sites mapping Web server. Results from these analyses placed CSTF2T on chromosome 10 at 4.19 cR from WI-8929 and 5.23 cR from WI-4701 (LOD 0.14 relative to most likely). This makes the approximate cytogenetic position of CSTF2T at 10q22–23, based in annexin A11 (10q22.3–23.1), retinal G protein coupled receptor (RGR, 10q23)) and lung surfactant protein D (10q23.3).

Example 24

Characterization of CSTF2T

Figure 2A:
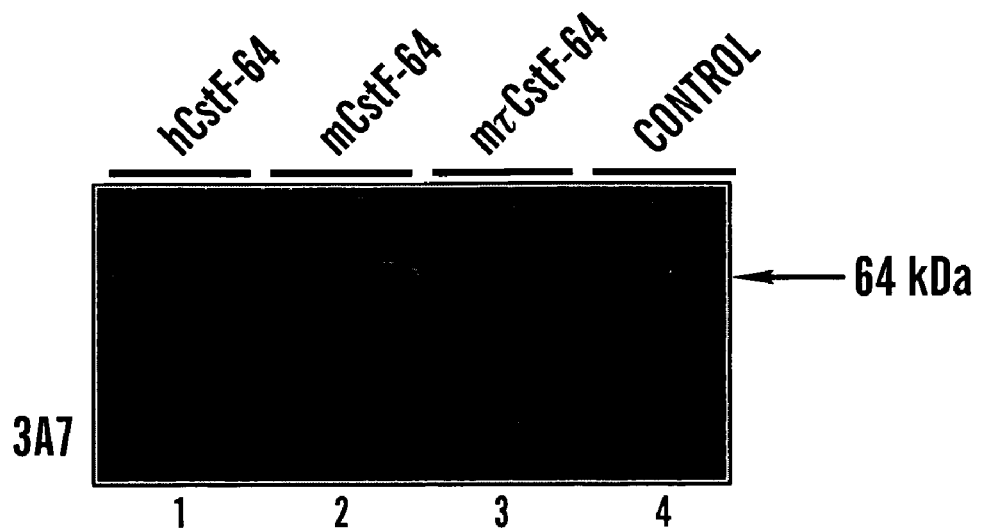
FIGS. 2A–B are SDS-PAGE electrophoresis gels showing antibody recognition of the protein encoded by mτCstF-64. Coupled transcription-translation extracts were programmed with cDNA clones of hCstF-64 (lane 1), mCstF-64 (lane 2), mτCstF-64 (lane 3), or pBluescript SK– (control, lane 4). Proteins were separated by 10% SDS-PAGE and immunoblots incubated with either the 3A7 monoclonal antibody, shown in FIG. 2A, or the 6A9 monoclonal antibody, shown in FIG. 2B.
Figure 2B:
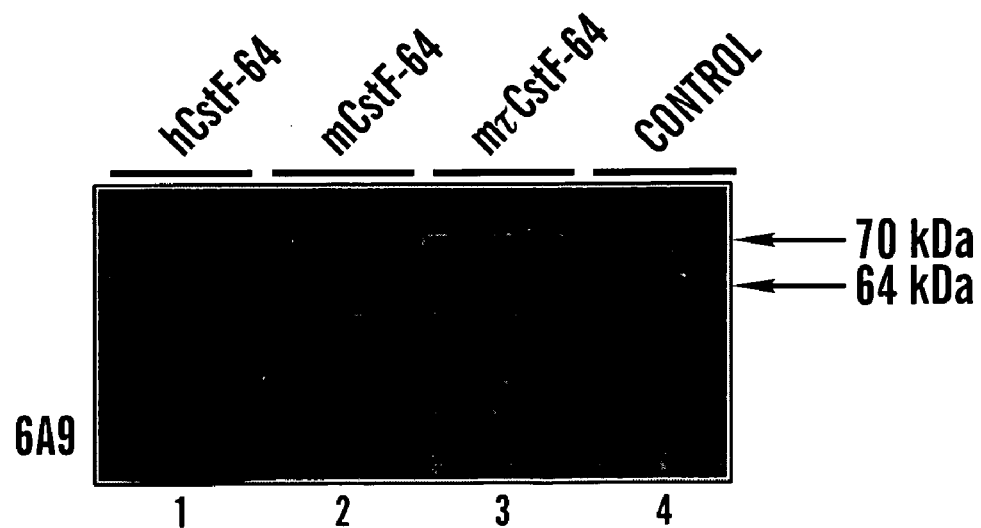

The cloning, sequencing, and gene mapping of a human cDNA that is greatly similar to mouse τCstF-64 (Cstf2t, Dass et al., "The Gene for a Variant Form of the Polyadenylation Protein CstF-64 is on Chromosome 19 and is Expressed in Pachytene Spermatocytes in Mice," *J. Biol. Chem.* 276:8044–8050 (2001), which is hereby incorporated by reference in its entirety), has been described and it was concluded that hτCstF-64 (CSTF2T) encodes the human ortholog of mτCstF-64. The human τCstF-64 protein differed greatly from the human somatic CstF-64, and was much more similar to the mouse τCstF-64. Human τCstF-64 and mouse τCstF-64 also shared the peculiar reactivity with the 3A7 and 6A9 monoclonal antibodies, as shown in FIGS. 2A–B, consistent with the conclusion that these genes are orthologous. Human τCstF-64 was found in a cDNA library representing human testicular mRNA, suggesting strongly that hτCstF-64 is expressed in that tissue, most likely in germ cells. Finally, while greatly resembling the other CstF-64 homologs, hτCstF-64 has several features that are unique to the τCstF-64s including a proline→serine substitution in the RNA-binding domain, two inserts relative to CstF-64, a reduced number of MEARA repeats, and amino acid substitutions throughout the protein, as shown in FIG. 4A and FIG. 6. Since the region of mouse chromosome 19 on which Cstf2t resides is homologous to both human chromosomes 9 and 10, it was determined the chromosome localization of CSTF2T by two methods. Both methods were consistent with a localization of CSTF2T to 10q22–23.

CSTF2, the gene for the somatic CstF-64, is on the X-chromosome (Wallace et al., "Two Distinct Forms of the 64,000 $M_r$ Protein of the Cleavage Stimulation Factor are Expressed in Mouse Male Germ Cells," *Proc. Natl. Acad. Sci. USA* 96:6763–6768 (1999), which is hereby incorporated by reference in its entirety). Since the CSTF2T expression is likely necessary in postmeiotic male germ cells because of X-chromosomal inactivation of CSTF2 during the pachytene phase of spermatogenesis, evidence of the variant CstF-64 in human testis suggests a common mechanism of polyadenylation via the activation of an autosomal paralog persists in evolution of both mice and humans. Thus, it is believed that activation of the autosomal CSTF2T gene during meiosis provides an alternative source of CstF-64 protein, which is essential for normal transcription and mRNA processing in these cells. τCstF-64 could play several different roles: it allows normal gene expression to occur in the absence of CstF-64 during pachytene of meiosis, it favors the use of alternative and non-canonical polyadenylation signals in germ cells, thereby increasing the complexity and diversity of transcripts present in those cells, and it provides a mechanism to activate several key meiotic genes (for instance, CREMτ (Foulkes et al., "Developmental Switch of CREM Function During Spermatogenesis: From Antagonist to Activator," *Nature* 355:80–84 (1992), which is hereby incorporated by reference in its entirety) that are essential for the normal progression of spermatogenesis.

The region 10q22–23 has been largely sequenced by the Human Genome Sequencing project (International Human Genome Sequencing Consortium, "Initial Sequencing and Analysis of the Human Genome," *Nature* 409:860–921 (2001); Venter et al., "The Sequence of the Human Genome," *Science* 291:1304–1351 (2001), which are hereby incorporated by reference in their entirety), allowing comparison of the hτCstF-64 cDNA to its encoding gene. Alignment of the hτCstF-64 cDNA with 10q22–23 (Altschul et al., "Gapped BLAST and PSI-BLAST: a New Generation of Protein Database Search Programs," *Nucl. Acids Res.* 25:3389–3402 (1997), which is hereby incorporated by reference in its entirety) revealed that CSTF2T gene lacks introns. Similarly, the gene for the mouse τCstF-64 lacks introns. Therefore, the autosomal τCstF-64 paralogs of the X-linked CstF-64 probably arose as a consequence of retroviral insertion (or retroposition) rather than gene duplication. Retroposition is also the proposed mode of evolution of germ cell-expressed autosomal paralogs of other X-chromosomal genes (Wang et al., "An Abundance of X-Linked Genes Expressed in Spermatogonia," *Nature Genetics* 27:422–426 (2001), which is hereby incorporated by reference in its entirety) like phosphoglycerate kinase, glucose-6-phosphate dehydrogenase, the pyruvate dehydrogenase E1 alpha subunit, the eukaryotic initiation factor-2γ, XAP-5, the heterogeneous nuclear ribonucleoprotein G, RBMXL9, and TAF(II)250 (McCarrey et al., "Human testis-specific PGK gene lacks introns and possesses characteristics of a processed gene," *Nature* 326:501–504 (1987)); Boer et al., "The Testis-Specific Phosphoglycerate Kinase Gene pgk-2 is a Recruited Retroposon," *Molecular Cell Biology* 7:3107–3112 (1987); Dahl et al., "A Testis-Specific Form of the Human Pyruvate Dehydrogenase E1 Alpha Subunit is Coded for by an Intronless Gene on Chromosome 4," *Genomics* 8:225–232 (1990); Hendriksen et al., "Testis-Specific Expression of a Functional Retroposon Encoding Glucose-6-Phosphate Dehydrogenase in the Mouse," *Genomics* 41:350–359 (1997); Ehrmann et al., "Characterization of Genes Encoding Translation Initiation Factor eIF-2γ in Mouse and Human: Sex Chromosome Localization, Escape from X-Inactivation and Evolution," *Hum. Mol. Genet.* 7:1725–1737 (1998); Sedlacek et al, "Human and Mouse XAP-5 and XAP-5-Like (X5L) Genes: Identification of an Ancient Functional Retroposon Differentially Expressed in Testis," *Genomics* 61:125–132 (1999); Elliott et al., "An Evolutionarily Conserved Germ Cell-Specific hnRNP is Encoded by a Retrotransposed Gene," *Hum. Mol. Genet.* 9:2117–2124 (2000); Lingenfelter et al., "Expression and Conservation of Processed Copies of the RBMX Gene," *Mamm. Gen.* 12:538–545 (2001); Wang et al., "Functional Substitution for TAF(II)250 by a Retroposed Homolog That is Expressed in Human Spermatogenesis," *Hum. Mol. Genet.* 11:2341–2346 (2002), which are hereby incorporated by reference in their entirety). This finding further implies that the event leading to activation of the retroposed variant of CstF-64 took place before the divergence of rodents and primates.

Prior to the cloning of the human τCstF-64 cDNA, the sequence similarity between mouse τCstF-64 and KIAA0689 (Ishikawa et al., "Prediction of the Coding Sequences of Unidentified Human Genes. X. The Complete Sequences of 100 New cDNA Clones From Brain Which Can Code for Large Proteins in Vitro," *DNA Res.* 5:169–176 (1998), which is hereby incorporated by reference in its entirety) suggested that the latter was the likely human homolog of τCstF-64 (Dass et al., "The Gene for a Variant Form of the Polyadenylation Protein CstF-64 is on Chromosome 19 and is Expressed in Pachytene Spermatocytes in Mice," *J. Biol. Chem.* 276:8044–8050 (2001), which is hereby incorporated by reference in its entirety). Human τCstF-64 is identical to KIAA0689 in its coding region, but it is truncated in its 3' UTR, suggesting that human τCstF-64 is alternatively polyadenylated in some tissues. Since KIAA0689 was first found in brain, expression of human τCstF-64 in brain and testis corresponds to the sites of protein expression identified in mouse (Wallace et al., "Two Distinct Forms of the 64,000 $M_r$ Protein of the Cleavage Stimulation Factor are Expressed in Mouse Male Germ Cells," *Proc. Natl. Acad. Sci. USA* 96:6763–6768 (1999), which is hereby incorporated by reference in its entirety). This provides further evidence that hτCstF-64 is the functional ortholog of mτCstF-64. Interestingly, these data strongly support mapping of CSTF2T to 10q22–23, shown in FIG. 5, while Ishikawa et al. report it to map to chromosome 5 (Ishikawa et al., "Prediction of the Coding Sequences of Unidentified Human Genes. X. The Complete Sequences of 100 New cDNA Clones From Brain Which Can Code for Large Proteins in Vitro," *DNA Res.* 5:169–176 (1998), which is hereby incorporated by reference in its entirety). Similarly, the genes for two other important polyadenylation proteins, the 160,000 $M_r$ (CPSF1) and 100,000 $M_r$ (CPSF2) subunits of the cleavage and polyadenylation specificity factor have been assigned to human chromosomes 8q24.23 (CPSF1, Samiotaki et al., "Assignment of the 160-kDa Subunit of Cleavage and Polyadenylation Specificity Factor (CPSF1) to Human Chromosome 8q24.23 by Radiation Hybrid Mapping," *Cytogenet. Cell. Genet.* 90:234–235 (2000), which is hereby incorporated by reference in its entirety) and 14q31.3 (CPSF2, Samiotaki et al., "Assignment of the 100-kDa Subunit of Cleavage and Polyadenylation Specificity Factor (CPSF2) to Human Chromosome 14q31.3 by Radiation Hybrid Mapping," *Cytogenet. Cell. Genet.* 90:328–329 (2000), which is hereby incorporated by reference in its entirety), and are unlinked to CSTF2 or CSTF2T Finally, it is noted that an oligospermic male with a reciprocal translocation in 10q22 [XY, t(10:11)(q22:q25)] has been reported (Bourrouillou et al., "Anomalies Chromosomiques Chez les Hommes Steriles, Etude Chez 241 Sujets. [Chromosome Aberrations in Sterile Males. Study of 241 Cases (Letter)]," *Nouv Presse Med* 7:3777 (1978), which is hereby incorporated by reference in its entirety). This suggests the hypothesis that lesions in CSTF2T, while not lethal, can lead to decreased fertility in human males. To begin to address this possibility, τCstF-64 in human tissues is being examined including testicular germ cells. Future studies will continue to examine these and other possibilities.

Although preferred embodiments have been depicted and described in detail herein, it will be apparent to those skilled in the relevant art that various modifications, additions, substitutions, and the like can be made without departing from the spirit of the invention and these are therefore considered to be within the scope of the invention as defined in the claims which follow.

What is claimed:

1. An isolated human nucleic acid molecule encoding a protein or polypeptide which controls RNA polyadenylation, wherein the nucleic acid molecule is a variant of a somatic nucleic acid molecule, is functional when the somatic nucleic acid molecule is not functional, and has the nucleotide sequence of SEQ ID NO: 1.

2. A nucleic acid construct comprising:
   the nucleic acid molecule according to claim 1;
   an operably linked DNA promoter; and
   an operably linked 3' regulatory region.

3. An expression system comprising:
   the nucleic acid construct according to claim 2.

4. A host cell transduced with the nucleic acid construct according to claim 2.

5. The host cell according to claim 4, wherein the cell is selected from the group consisting of a bacterial cell, a yeast cell, and a mammalian cell.

6. The host cell according to claim 5, wherein the cell is a mammalian cell.

7. The host cell according to claim 6, wherein the mammalian cell is a human cell.

8. A virus comprising the nucleic acid construct according to claim 2.

* * * * *

SEQUENCE LISTING

<160> NUMBER OF SEQ ID NOS: 10

<210> SEQ ID NO 1
<211> LENGTH: 2341
<212> TYPE: DNA
<213> ORGANISM: Homo sapiens

<400> SEQUENCE: 1

```
ggcacgagcc gctatcggct gtctgcacaa ccggaatcat gtcgagtttg gcggtgagag      60
acccggcaat ggatcgatca ctgcgttccg tgttcgtggg aacattcca tatgaggcaa      120 ctgaggagca gttaaaggac attttctcgg aggttggttc tgttgtcagt ttccggctgg      180
tatacgatag agagacggga aaacccaagg gctatggctt ctgcgaatac caagaccagg      240
agaccgcgct tagtgccatg cggaacctca atgggcggga gttcagtggg agagcgcttc      300
gggtggacaa tgctgccagt gaaaagaata aggaggagtt aaagagcctt gggcctgcag      360
cgcccattat tgactcaccc tatggggatc ccatcgatcc agaagatgcc cctgaatcga      420
ttaccagagc agtagccagt ctccccccgg agcagatgtt tgagctgatg aagcagatga      480
agctctgtgt ccaaaacagc caccaggaag ctcgaaacat gttacttcaa aatccacaac      540
tggcttatgc actgttgcag gcacaagtag tgatgagaat catggatcca gagattgctc      600
tgaaaattct gcatcggaag atacatgtca caccactgat cccaggcaaa tctcagtctg      660
tgtctgtctc tggccctggc cctggccctg gccctgggct ctgcccagga cctaatgttc      720
tgctgaacca gcagaatcct ccagctcctc agcctcagca tttggctaga agacctgtga      780
aggacattcc tcctctgatg cagactccta tccagggtgg aattccagct ccagggccaa      840
taccagctgc agttcccgga gctggtcctg gttccttaac tcctggagga gcaatgcagc      900
cccaacttgg aatgccaggg gttggcccag tgcctttaga gcggggacaa gtgcagatgt      960
cagatcctag agctcctata cctcgcggac ccgtgactcc tggtggtctg cctcctcgag      1020
gactgttagg agatgctcca aatgacccac gtggagggac tttgctttca gtcactggag      1080
aagtggagcc cagaggttat ctgggtccac cccatcaggg tccccccatg catcatgcct      1140
ctggtcatga cactcgtggc ccttcctcac atgagatgag gggagggcca ttaggagatc      1200
ccagactgct aattggagag cccagaggcc ccatgataga tcaaagggt ctacctatgg      1260 atggtagagg tggtagagat tctcgagcga tggagactcg tgccatggaa actgaggtct      1320
tagagacacg tgtaatggag aggagaggaa tggagacctg tgcgatggaa accagaggga      1380
tggaagcaag gggcatggat gcaagaggat tggagatgag gggccctgtc cccagttcaa      1440
gaggccctat gactggtgga attcagggtc ctggtcccat taatataggg gcaggtggcc      1500
ctcctcaggg acccagacag gtcccaggca tttcagggct ggggaatcct ggagctggta      1560
tgcagggtac aggcatacaa ggaacaggca tgcagggagc aggcatacaa ggaggaggga      1620
tgcagggggc aggcatacaa ggagtcagta tacaaggagg aggtatacaa ggaggaggta      1680 tacaggggc aagcaagcaa ggtggaagcc agcctagcag ttttagtcct gggcagagcc      1740
```

```
aggtcactcc acaggatcag gagaaggcag ctttgatcat gcaggttctt caactgactg    1800
cagatcagat tgccatgctg ccccctgagc aaaggcagag tatcctgatt ttaaaggaac    1860
aaatccagaa atccactgga gcgtcttgaa aggttttaga aaatatttgg ctgtagtctc    1920 aaatttatt  ctgtagcatg gagaatgggt gcaaaaagct gacttctgta tccccacact    1980
tggattaggg tttccctcct cctagaacct aatcttattt tttgttcttt ttctttcttt    2040
ctgttttcct ttttttttaa ttgagggtgg ggggaggagg gagtgcgtct gttcacttta    2100
agttacttta aataactct  gaacatgatt atattatgcc aaataagatt acaaagaata    2160
agcagcaata ttgaagcatc tacagtatgt taactacatt ttttaaatgt cgagtaaaac    2220
ttcgtgaaaa ctgctcataa agactaaaag ttgacctgtt aaaacgttaa tgtactaaga    2280 tagtttaag  attttggtt  gtataacaaa ataaagttt  acccaaaaaa aaaaaaaaaa    2340
a                                                                    2341
```

<210> SEQ ID NO 2
<211> LENGTH: 616
<212> TYPE: PRT
<213> ORGANISM: Homo sapiens

<400> SEQUENCE: 2

```
Met Ser Ser Leu Ala Val Arg Asp Pro Ala Met Asp Arg Ser Leu Arg
 1               5                  10                  15

Ser Val Phe Val Gly Asn Ile Pro Tyr Glu Ala Thr Glu Glu Gln Leu
            20                  25                  30

Lys Asp Ile Phe Ser Glu Val Gly Ser Val Val Ser Phe Arg Leu Val
        35                  40                  45

Tyr Asp Arg Glu Thr Gly Lys Pro Lys Gly Tyr Gly Phe Cys Glu Tyr
    50                  55                  60

Gln Asp Gln Glu Thr Ala Leu Ser Ala Met Arg Asn Leu Asn Gly Arg
65                  70                  75                  80

Glu Phe Ser Gly Arg Ala Leu Arg Val Asp Asn Ala Ala Ser Glu Lys
                85                  90                  95

Asn Lys Glu Glu Leu Lys Ser Leu Gly Pro Ala Pro Ile Ile Asp
            100                 105                 110

Ser Pro Tyr Gly Asp Pro Ile Asp Pro Glu Asp Ala Pro Glu Ser Ile
        115                 120                 125

Thr Arg Ala Val Ala Ser Leu Pro Pro Glu Gln Met Phe Glu Leu Met
    130                 135                 140

Lys Gln Met Lys Leu Cys Val Gln Asn Ser His Gln Glu Ala Arg Asn
145                 150                 155                 160

Met Leu Leu Gln Asn Pro Gln Leu Ala Tyr Ala Leu Leu Gln Ala Gln
                165                 170                 175

Val Val Met Arg Ile Met Asp Pro Glu Ile Ala Leu Lys Ile Leu His
            180                 185                 190

Arg Lys Ile His Val Thr Pro Leu Ile Pro Gly Lys Ser Gln Ser Val
        195                 200                 205

Ser Val Ser Gly Pro Gly Pro Gly Pro Gly Leu Cys Pro Gly
    210                 215                 220

Pro Asn Val Leu Leu Asn Gln Gln Asn Pro Ala Pro Gln Pro Gln
225                 230                 235                 240

His Leu Ala Arg Arg Pro Val Lys Asp Ile Pro Pro Leu Met Gln Thr
                245                 250                 255
```

```
Pro Ile Gln Gly Gly Ile Pro Ala Pro Gly Pro Ile Pro Ala Ala Val
            260                 265                 270
Pro Gly Ala Gly Pro Gly Ser Leu Thr Pro Gly Gly Ala Met Gln Pro
            275                 280                 285
Gln Leu Gly Met Pro Gly Val Gly Pro Val Pro Leu Glu Arg Gly Gln
            290                 295                 300
Val Gln Met Ser Asp Pro Arg Ala Pro Ile Pro Arg Gly Pro Val Thr
305                 310                 315                 320
Pro Gly Gly Leu Pro Pro Arg Gly Leu Leu Gly Asp Ala Pro Asn Asp
            325                 330                 335
Pro Arg Gly Gly Thr Leu Leu Ser Val Thr Gly Glu Val Glu Pro Arg
            340                 345                 350
Gly Tyr Leu Gly Pro Pro His Gln Gly Pro Pro Met His His Ala Ser
            355                 360                 365
Gly His Asp Thr Arg Gly Pro Ser Ser His Glu Met Arg Gly Gly Pro
            370                 375                 380
Leu Gly Asp Pro Arg Leu Leu Ile Gly Glu Pro Arg Gly Pro Met Ile
385                 390                 395                 400
Asp Gln Arg Gly Leu Pro Met Asp Gly Arg Gly Gly Arg Asp Ser Arg
            405                 410                 415
Ala Met Glu Thr Arg Ala Met Glu Thr Glu Val Leu Glu Thr Arg Val
            420                 425                 430
Met Glu Arg Arg Gly Met Glu Thr Cys Ala Met Glu Thr Arg Gly Met
            435                 440                 445
Glu Ala Arg Gly Met Asp Ala Arg Gly Leu Glu Met Arg Gly Pro Val
            450                 455                 460
Pro Ser Ser Arg Gly Pro Met Thr Gly Gly Ile Gln Gly Pro Gly Pro
465                 470                 475                 480
Ile Asn Ile Gly Ala Gly Gly Pro Pro Gln Gly Pro Arg Gln Val Pro
            485                 490                 495
Gly Ile Ser Gly Val Gly Asn Pro Gly Ala Gly Met Gln Gly Thr Gly
            500                 505                 510
Ile Gln Gly Thr Gly Met Gln Gly Ala Gly Ile Gln Gly Gly Met
            515                 520                 525
Gln Gly Ala Gly Ile Gln Gly Val Ser Ile Gln Gly Gly Gly Ile Gln
            530                 535                 540
Gly Gly Gly Ile Gln Gly Ala Ser Lys Gln Gly Gly Ser Gln Pro Ser
545                 550                 555                 560
Ser Phe Ser Pro Gly Gln Ser Gln Val Thr Pro Gln Asp Gln Glu Lys
            565                 570                 575
Ala Ala Leu Ile Met Gln Val Leu Gln Leu Thr Ala Asp Gln Ile Ala
            580                 585                 590
Met Leu Pro Pro Glu Gln Arg Gln Ser Ile Leu Ile Leu Lys Glu Gln
            595                 600                 605
Ile Gln Lys Ser Thr Gly Ala Ser
610                 615

<210> SEQ ID NO 3
<211> LENGTH: 3611
<212> TYPE: DNA
<213> ORGANISM: Mouse

<400> SEQUENCE: 3
gaattcggca cgaggtggtt cgccagagga cgacccttag acgaattcaa tctccgctgt    60
```

```
cctctcggca gcaatcatgt cgagtttggc ggtcagagac ccagccatgg atcgatcgct      120
gcgttcggtg ttcgtgggga acattccgta tgaggcgacg gaggagcagt taaaggacat      180
tttctcagag gttggttcag ttgtcagttt ccgtctcgtc tacgatagag agactgggaa      240
gcccaagggt tatggcttct gcgagtacca agaccaggag actgcgctca gtgccatgcg      300
aaacctcaat gggcgagagt ttagtgggag agcgcttcgg gtggacaatg ccgccagcga      360
aaagaacaag gaggagttaa agagcttagg cccggcggcc cccatcattg actccccta       420 tggggaccct atcgacccag aagatgctcc agaatcgatt actagagcag tcgccagctt      480 gccccccagag cagatgtttg agctcatgaa gcagatgaag ttgtgtgtcc agaacagtca     540
ccaggaagct cgaaacatgc tacttcagaa cccacagttg gcgtatgctt tgctgcaggc      600
acaagtggtg atgagaatca tggatccaga gattgcactg aaaattttgc atcgtaagat      660
acatgtcaca ccactgatcc caggcaaatc tcagccggtc tctgggcctg gcctggtggg      720
ctgggctagt gggctggcgg ctggcccggc ccctgcccct ggcctctgcc cgggacctaa      780
cgtcatgttg aaccaacaga atcctcctgc ccctcagcct cagcatctgc caagaagacc      840
tgtgaaggac attccacctc tgatgcagac ctctatccag ggaggaattc cagctccggg      900
gccaatacca gctgcagttc ctggacctgg acctggttcc ttaactccag gaggagcaat      960
gcagccacaa gttggcatgc cagtggttgg tccagtgccc ctggagcgag acagatgca     1020 gatatcagat cctagacctc cgatgcctcg tggacccatg ccttctggtg gcatacctcc     1080
tcgaggacta ctgggagatg ctccaaatga cccacgtgga gggactttgc tctcagtgac     1140
tggagaagta gagcccaggg gctatatggg accacccat cagggtcctc caatgcatca     1200
tggtcatgac aaccgtggcc ctgcctcaca tgatatgaga ggaggaccat tggcagcaga     1260
tcccagaatg ctaattggag agcccagagg tcccatgata gatcagagag gtctacctat     1320
ggatggtaga ggaggtagag aatctcgagg gatggagact cggcccatgg aaactgaggt     1380
cttggagcca cgaggaatgg agagaaggat ggagacctgc gcgatggaaa ccagaggcat     1440
ggatgcaaga ggactagaga tgaggggccc tggccctagt tccagaggtc cgatgactgg     1500
tggaatccag ggtcctggcc ctattaatat gggggcaggt ggccctcagg gacctagaca     1560
ggttccaaat attgcaggag tgggaaatcc tggaggtacc atgcaggggg caggtataca     1620
aggaggaggg atgcagggag caggtatgca aggaggaggg atgcaaggag caggcatgca     1680
aggaggaggg atgcagggag ctggcatgca agcaggatg caggggagcta gcatgcaagg     1740 agggatgcag ggagctggca tgcaaggagc cagtaagcaa ggtggaggcc agcctagcag     1800 ttttagcct gggcaaagcc aggtaactcc acaagatcaa gaaaaagcag ctttgatcat      1860
gcaggttctc cagctgactg cggatcagat tgccatgctg cctcccgaac aaaggcagag     1920
cattttgatt ttaaaggaac aaatccagaa atccactggg gcttcttgaa tggttttcaa      1980
ctaagaagca cttagttact ccttcagagt ttattctgtg gcatgaagtg gtgcaaaaag     2040
ctgtcttctg tgttcgcaca ctttaaccat ttaaggtttc cttctcccta gatcttaatc     2100
tttcttctag tcctgtcact ttctgcttcc cttttagctt tttgatggag ttatgcgagt      2160
ggaaggagtg ggcctgttca ctttgtcact gttactctac cacgtaccct gaaaataact     2220
acatcatcca ccaagtaagg ctatgaggaa gatgcaggag gaataacatg tctgcacttt     2280
gttaactgcg tctttaaaaa tcccgagtaa gctgggaact acataaaat tgaaagtgac      2340 ttgttacagt attgatatac taagatggtt taaaggtttt tggttgtata ttaactgaat     2400
gtcagcatct taagatacac ttttggtaa accaaaatac tgtagagtaa taagattaat       2460
```

```
gtttagttat ttttggaatta tttttgaaata ttggagctaa cagtctgtgg tgtagatgta   2520
gggttttttt tgttttttgtt ttttttttttt taagcattgt tatctgtaaa aaggtaatt    2580 tcatttacct gacttttttg agacaactaa tattcttgcc tggtcccacc tggtgatttt    2640
gcagaatagt tgtagtgtca gctgaattat ataaagccgc ctctgaggag actcaagtga   2700
tttcctaata catttctcta aaaaaattct taagcaccaa gtctggttgt aagtagtttt   2760
ttcatgtcat ctgaaaatag cagttagaca tggggtcgga cttcttgag taatggaggg    2820 tttttcagta aagctcccac ccaggttctt gataaaccac tatccatacg cagatggaat   2880
ccatttggtc agcaggaatc agaagttaaa aaatcttagt cttcgaattt tgacgtgtct   2940
tacagtttga taactttcac aaagtacttt cctgccatca gcttaactag aactgaggcc   3000
caagtgatct gacagctctg ctcaacttag tattttattt cttagaactc tcaagagcca   3060
tttggtcata acatacattc ctatcagatg tgttttaaaa taaggagtgt ggaatttaat   3120
acatttcctt tagagctacc atactatttt ttgacattaa gtgtgtggca cctagacacc   3180
atgtcatatc tagttaatga gcagaaacaa gcacaagttc ccacttgacc aagtgatagt   3240
cctctgtagg aaactaacta cccagctaca gagggaagag tagccttagg gagagagctg   3300
acccaagggt ctactttgtc cttggaaagt ttgagcattt tcagtgtaca gagttttcat   3360
tcctaggcta ttttccatcg acttagtttt ttgtgctagt gttaaactct ctgtggtttc   3420
ctctgcttct cctttgctga agttggtttg tgttttgtac ttttgtgcta gttctggcta   3480
attccaattg cttgctttcg aaattgcggt tgctagccca aaacttctta tagtctttgt   3540
tataagaaaa tctctgcatt gtttaatgaa aattaaataa aaaggttgta taattaaaaa   3600 aaaaaaaaa a                                                          3611

<210> SEQ ID NO 4
<211> LENGTH: 630
<212> TYPE: PRT
<213> ORGANISM: Mouse

<400> SEQUENCE: 4

Met Ser Ser Leu Ala Val Arg Asp Pro Ala Met Asp Arg Ser Leu Arg
 1               5                  10                  15

Ser Val Phe Val Gly Asn Ile Pro Tyr Glu Ala Thr Glu Glu Gln Leu
            20                  25                  30

Lys Asp Ile Phe Ser Glu Val Gly Ser Val Val Ser Phe Arg Leu Val
        35                  40                  45

Tyr Asp Arg Glu Thr Gly Lys Pro Lys Gly Tyr Gly Phe Cys Glu Tyr
    50                  55                  60

Gln Asp Gln Glu Thr Ala Leu Ser Ala Met Arg Asn Leu Asn Gly Arg
65                  70                  75                  80

Glu Phe Ser Gly Arg Ala Leu Arg Val Asp Asn Ala Ala Ser Glu Lys
                85                  90                  95

Asn Lys Glu Glu Leu Lys Ser Leu Gly Pro Ala Ala Pro Ile Ile Asp
            100                 105                 110

Ser Pro Tyr Gly Asp Pro Ile Asp Pro Glu Asp Ala Pro Glu Ser Ile
        115                 120                 125

Thr Arg Ala Val Ala Ser Leu Pro Pro Glu Gln Met Phe Glu Leu Met
    130                 135                 140

Lys Gln Met Lys Leu Cys Val Gln Asn Ser His Gln Glu Ala Arg Asn
145                 150                 155                 160
```

```
Met Leu Leu Gln Asn Pro Gln Leu Ala Tyr Ala Leu Leu Gln Ala Gln
                165                 170                 175

Val Val Met Arg Ile Met Asp Pro Glu Ile Ala Leu Lys Ile Leu His
            180                 185                 190

Arg Lys Ile His Val Thr Pro Leu Ile Pro Gly Lys Ser Gln Pro Val
        195                 200                 205

Ser Gly Pro Gly Leu Val Gly Trp Ala Ser Gly Leu Ala Ala Gly Pro
    210                 215                 220

Ala Pro Ala Pro Gly Leu Cys Pro Gly Pro Asn Val Met Leu Asn Gln
225                 230                 235                 240

Gln Asn Pro Pro Ala Pro Gln Pro Gln His Leu Pro Arg Arg Pro Val
                245                 250                 255

Lys Asp Ile Pro Pro Leu Met Gln Thr Ser Ile Gln Gly Gly Ile Pro
            260                 265                 270

Ala Pro Gly Pro Ile Pro Ala Ala Val Pro Gly Pro Gly Pro Gly Ser
        275                 280                 285

Leu Thr Pro Gly Gly Ala Met Gln Pro Gln Val Gly Met Pro Val Val
    290                 295                 300

Gly Pro Val Pro Leu Glu Arg Gly Gln Met Gln Ile Ser Asp Pro Arg
305                 310                 315                 320

Pro Pro Met Pro Arg Gly Pro Met Pro Ser Gly Gly Ile Pro Pro Arg
                325                 330                 335

Gly Leu Leu Gly Asp Ala Pro Asn Asp Pro Arg Gly Gly Thr Leu Leu
            340                 345                 350

Ser Val Thr Gly Glu Val Glu Pro Arg Gly Tyr Met Gly Pro Pro His
        355                 360                 365

Gln Gly Pro Pro Met His His Gly His Asp Asn Arg Gly Pro Ala Ser
    370                 375                 380

His Asp Met Arg Gly Gly Pro Leu Ala Ala Asp Pro Arg Met Leu Ile
385                 390                 395                 400

Gly Glu Pro Arg Gly Pro Met Ile Asp Gln Arg Gly Leu Pro Met Asp
                405                 410                 415

Gly Arg Gly Gly Arg Glu Ser Arg Gly Met Glu Thr Arg Pro Met Glu
            420                 425                 430

Thr Glu Val Leu Glu Pro Arg Gly Met Glu Arg Arg Met Glu Thr Cys
        435                 440                 445

Ala Met Glu Thr Arg Gly Met Asp Ala Arg Gly Leu Glu Met Arg Gly
    450                 455                 460

Pro Gly Pro Ser Ser Arg Gly Pro Met Thr Gly Gly Ile Gln Gly Pro
465                 470                 475                 480

Gly Pro Ile Asn Met Gly Ala Gly Gly Pro Gln Gly Arg Gln Val
                485                 490                 495

Pro Asn Ile Ala Gly Val Gly Asn Pro Gly Gly Thr Met Gln Gly Ala
            500                 505                 510

Gly Ile Gln Gly Gly Gly Met Gln Gly Ala Gly Met Gln Gly Gly Gly
        515                 520                 525

Met Gln Gly Ala Gly Met Gln Gly Gly Met Gln Gly Ala Gly Met
    530                 535                 540

Gln Ala Gly Met Gln Gly Ala Ser Met Gln Gly Met Gln Gly Ala
545                 550                 555                 560

Gly Met Gln Gly Ala Ser Lys Gln Gly Gly Gln Pro Ser Ser Phe
                565                 570                 575

Ser Pro Gly Gln Ser Gln Val Thr Pro Gln Asp Gln Glu Lys Ala Ala
```

|  | 580 | 585 | 590 |
| --- | --- | --- | --- |

Leu Ile Met Gln Val Leu Gln Leu Thr Ala Asp Gln Ile Ala Met Leu
               595                    600                  605

Pro Pro Glu Gln Arg Gln Ser Ile Leu Ile Leu Lys Glu Gln Ile Gln
  610                  615                 620

Lys Ser Thr Gly Ala Ser
625              630

```
<210> SEQ ID NO 5
<211> LENGTH: 23
<212> TYPE: DNA
<213> ORGANISM: Artificial Sequence
<220> FEATURE:
<223> OTHER INFORMATION: Description of Artificial Sequence:  Primer

<400> SEQUENCE: 5
gctctgccca ggacctaatg ttc                                             23

<210> SEQ ID NO 6
<211> LENGTH: 25
<212> TYPE: DNA
<213> ORGANISM: Artificial Sequence
<220> FEATURE:
<223> OTHER INFORMATION: Description of Artificial Sequence:  Primer

<400> SEQUENCE: 6
ttgtccccgc tctaaaggca ctggg                                           25

<210> SEQ ID NO 7
<211> LENGTH: 24
<212> TYPE: DNA
<213> ORGANISM: Artificial Sequence
<220> FEATURE:
<223> OTHER INFORMATION: Description of Artificial Sequence:  Primer

<400> SEQUENCE: 7
ccacgtggag ggactttgct ttca                                            24

<210> SEQ ID NO 8
<211> LENGTH: 23
<212> TYPE: DNA
<213> ORGANISM: Artificial Sequence
<220> FEATURE:
<223> OTHER INFORMATION: Description of Artificial Sequence:  Primer

<400> SEQUENCE: 8
tgccccttgc ttccatccct ctg                                             23

<210> SEQ ID NO 9
<211> LENGTH: 28
<212> TYPE: DNA
<213> ORGANISM: Artificial Sequence
<220> FEATURE:
<223> OTHER INFORMATION: Description of Artificial Sequence:  Primer
<220> FEATURE:
<221> NAME/KEY: unsure
<222> LOCATION: (5)
<223> OTHER INFORMATION: N at position 5 is inosine
<220> FEATURE:
<221> NAME/KEY: unsure
<222> LOCATION: (17)
<223> OTHER INFORMATION: N at position 17 is inosine
<220> FEATURE:
<221> NAME/KEY: unsure
<222> LOCATION: (20)
<223> OTHER INFORMATION: N at position 20 is inosine
```

```
<400> SEQUENCE: 9
caccncatca gggyccnccn atgcayca                                              28

<210> SEQ ID NO 10
<211> LENGTH: 29
<212> TYPE: DNA
<213> ORGANISM: Artificial Sequence
<220> FEATURE:
<223> OTHER INFORMATION: Description of Artificial Sequence:  Primer
<220> FEATURE:
<221> NAME/KEY: unsure
<222> LOCATION: (12)
<223> OTHER INFORMATION: N at position 12 is inosine
<220> FEATURE:
<221> NAME/KEY: unsure
<222> LOCATION: (18)
<223> OTHER INFORMATION: N at position 18 is inosine
<220> FEATURE:
<221> NAME/KEY: unsure
<222> LOCATION: (21)
<223> OTHER INFORMATION: N at position 21 is inosine

<400> SEQUENCE: 10
tgrtcygcag tnagytgnag nacctgcat                                             29
```